US010905468B2

(12) United States Patent
Ahluwalia

(10) Patent No.: US 10,905,468 B2
(45) Date of Patent: Feb. 2, 2021

(54) FORNIX MANIPULATOR

(71) Applicant: Prabhat K. Ahluwalia, Little Falls, NY (US)

(72) Inventor: Prabhat K. Ahluwalia, Little Falls, NY (US)

( * ) Notice: Subject to any disclaimer, the term of this patent is extended or adjusted under 35 U.S.C. 154(b) by 333 days.

(21) Appl. No.: 15/417,777

(22) Filed: Jan. 27, 2017

(65) Prior Publication Data

US 2017/0196592 A1   Jul. 13, 2017

Related U.S. Application Data

(63) Continuation of application No. 14/314,105, filed on Jun. 25, 2014, now Pat. No. 9,592,078, which is a continuation of application No. 13/091,517, filed on Apr. 21, 2011, now Pat. No. 8,770,200.

(60) Provisional application No. 61/326,326, filed on Apr. 21, 2010.

(51) Int. Cl.
*A61B 17/42* (2006.01)
*A61F 6/06* (2006.01)

(52) U.S. Cl.
CPC .............. *A61B 17/42* (2013.01); *A61F 6/06* (2013.01)

(58) Field of Classification Search
CPC ..... A61F 6/06; A61F 6/08; A61F 6/12; A61B 17/0218; A61B 17/42; A61B 17/4216; A61B 17/4225; A61B 17/4241; A61B 17/32; A61B 17/303; A61B 1/32; A61B 1/303
USPC ....... 128/830, 834, 837, 838, 839, 840, 841; 600/37, 201, 204; 606/119
See application file for complete search history.

(56) References Cited

U.S. PATENT DOCUMENTS

| | | | | |
|---|---|---|---|---|
| 5,392,764 A | * | 2/1995 | Swanson | A61B 1/32 600/187 |
| 6,773,418 B1 | * | 8/2004 | Sharrow | A61M 3/027 600/201 |
| 8,770,200 B2 | * | 7/2014 | Ahluwalia | A61F 6/06 128/830 |
| 2005/0124860 A1 | * | 6/2005 | Mohajer | A61B 1/00142 600/203 |
| 2008/0039864 A1 | * | 2/2008 | Feuer | A61B 17/4241 606/119 |
| 2008/0242919 A1 | * | 10/2008 | La Vean | A61F 6/08 600/35 |

* cited by examiner

*Primary Examiner* — Kari K Rodriquez
(74) *Attorney, Agent, or Firm* — Pierson Intellectual Property LLC

(57) ABSTRACT

A fornix manipulator includes a collar and stabilizer. The collar has a first end and a second end, the second end having an opening and diameter greater than the first end and the first end having an opening to receive a cervix into the collar. The stabilizer has a base portion defining a guide hole and a plurality of prongs extending from the base portion to contact the first end of the collar.

14 Claims, 33 Drawing Sheets

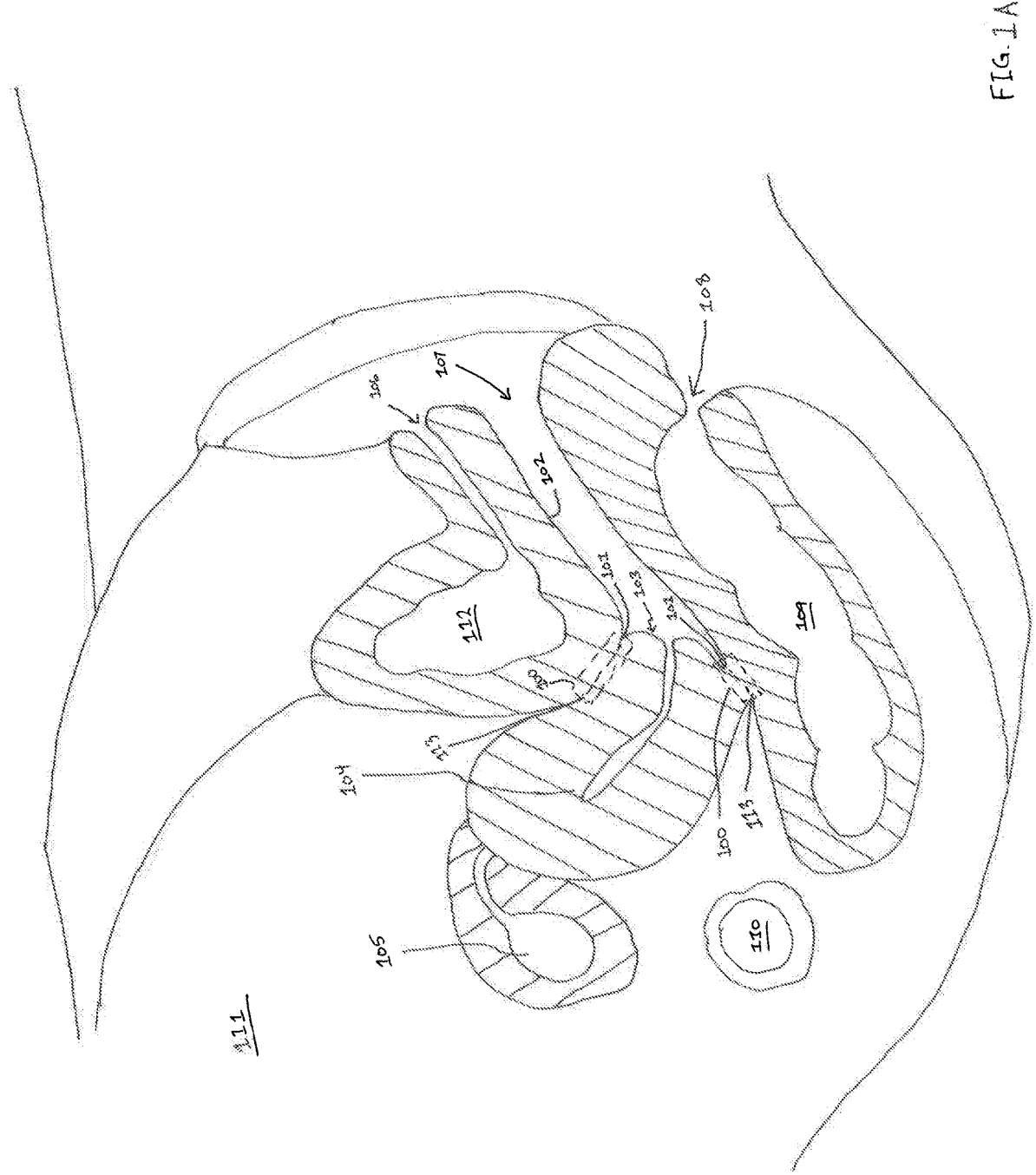

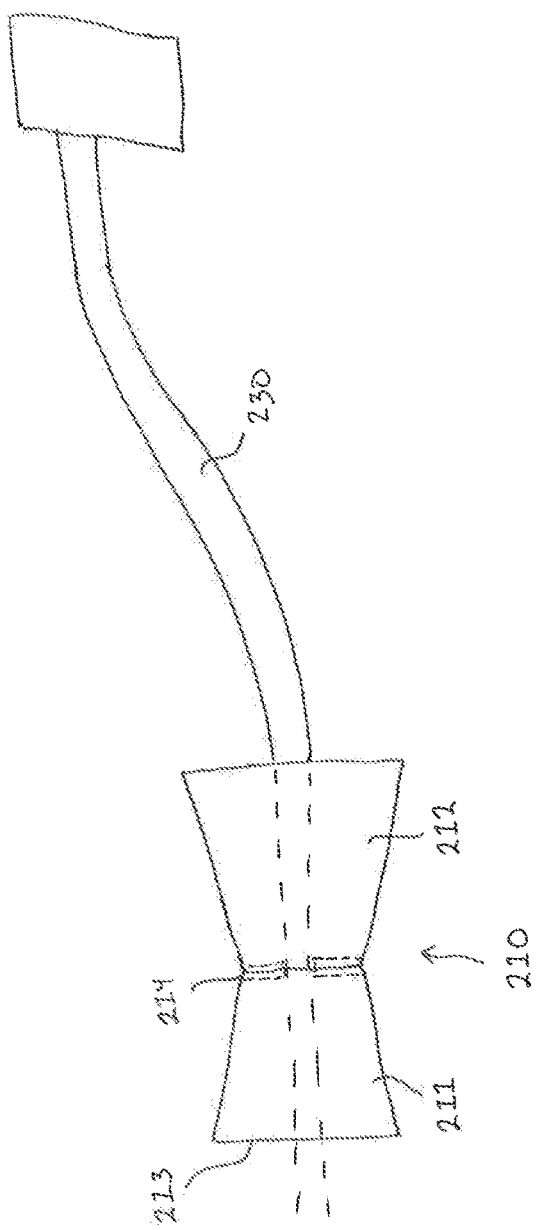

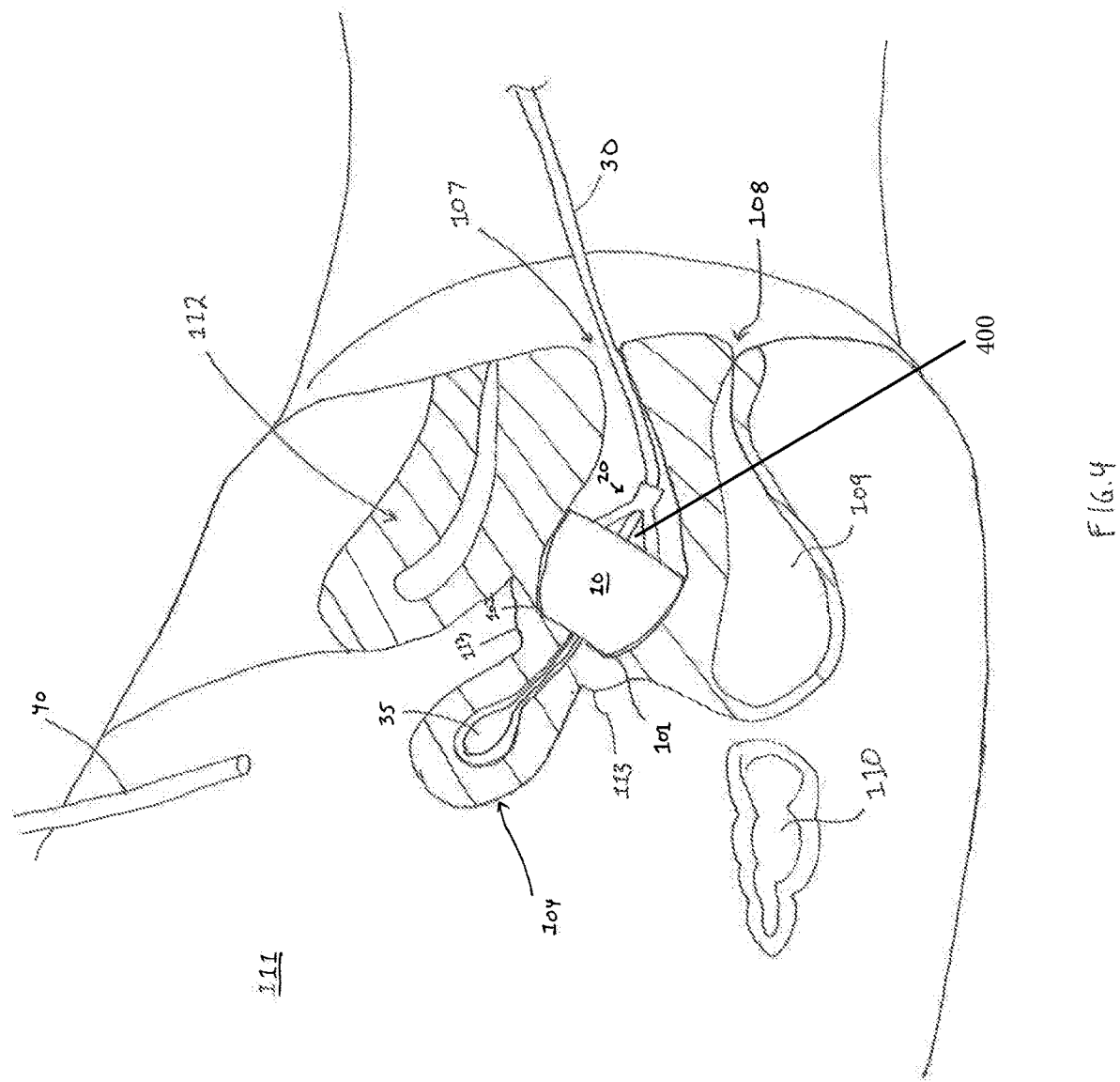

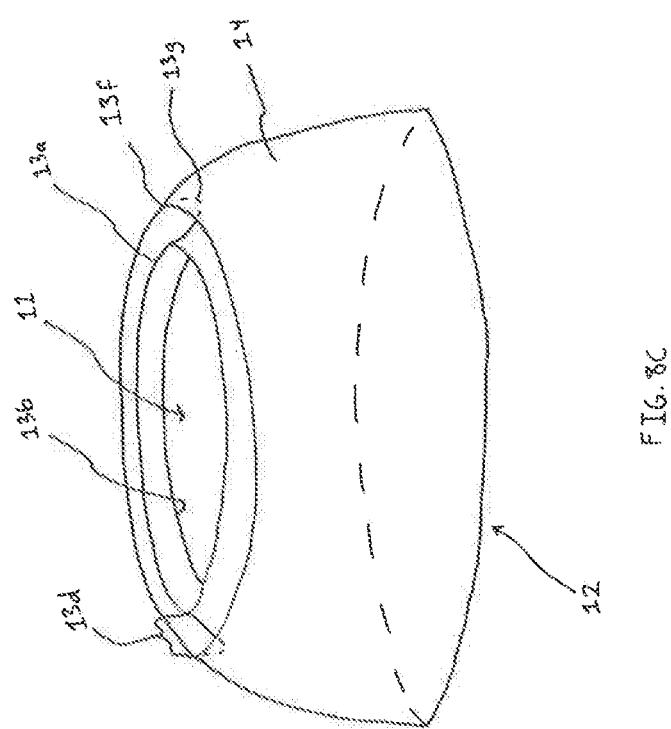

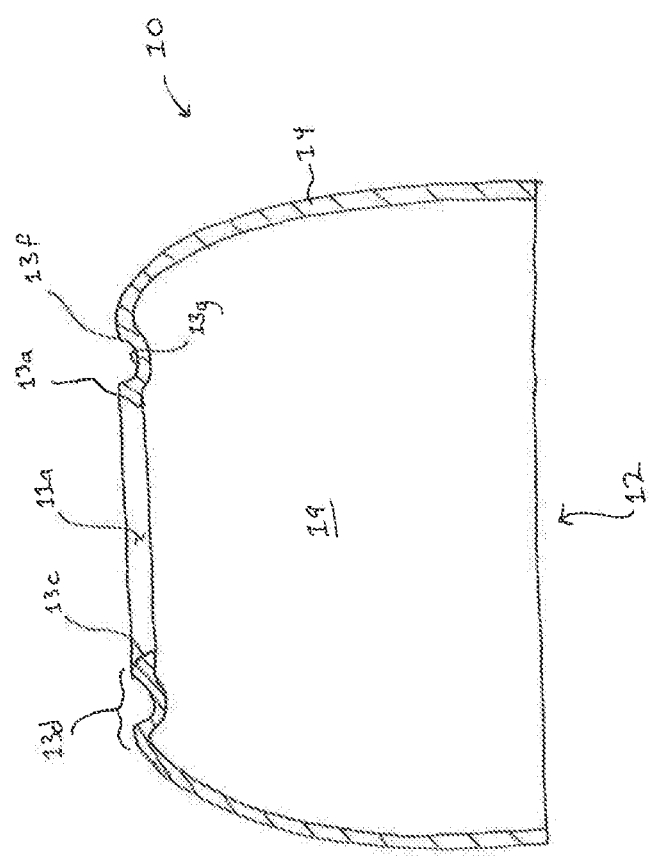

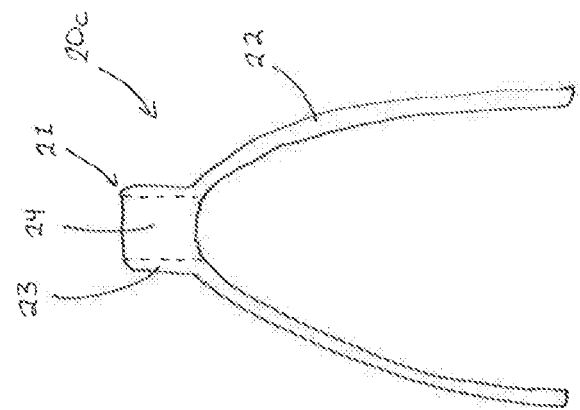
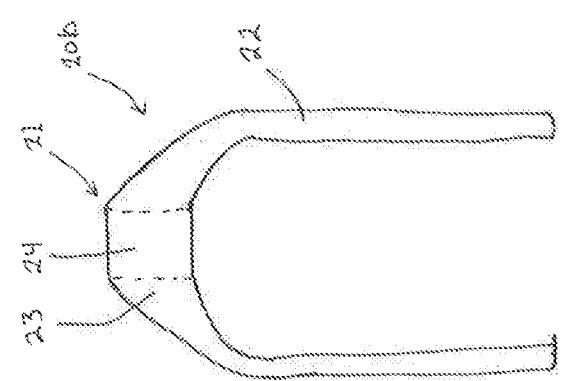
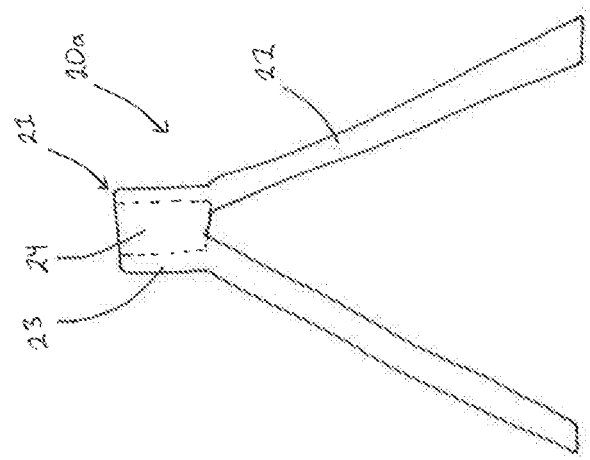
FIG. 9C
FIG. 9B
FIG. 9A

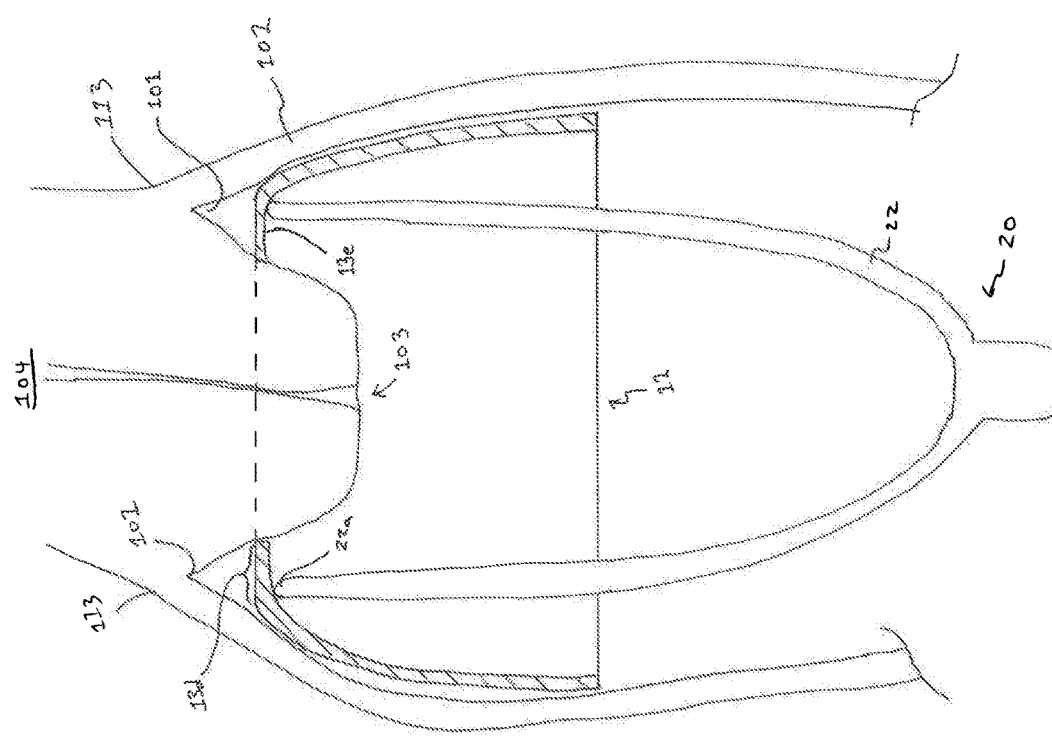

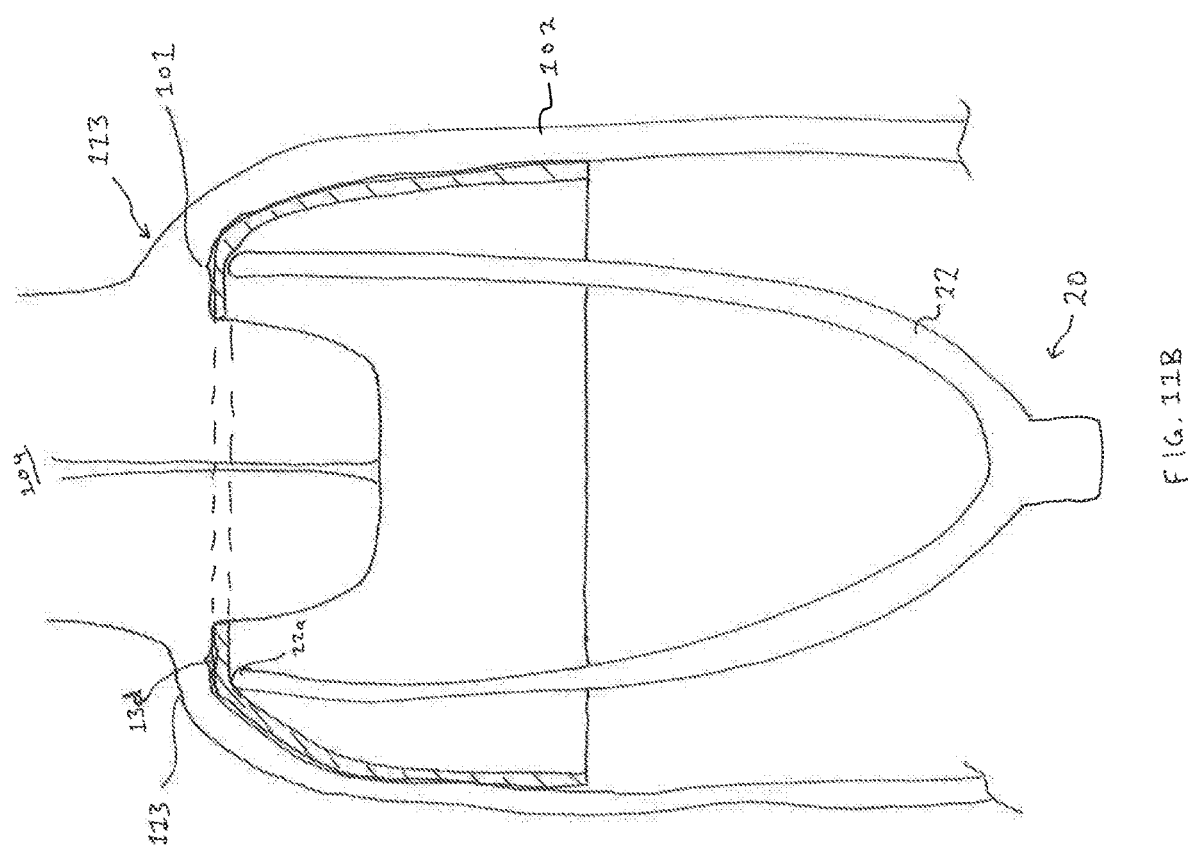

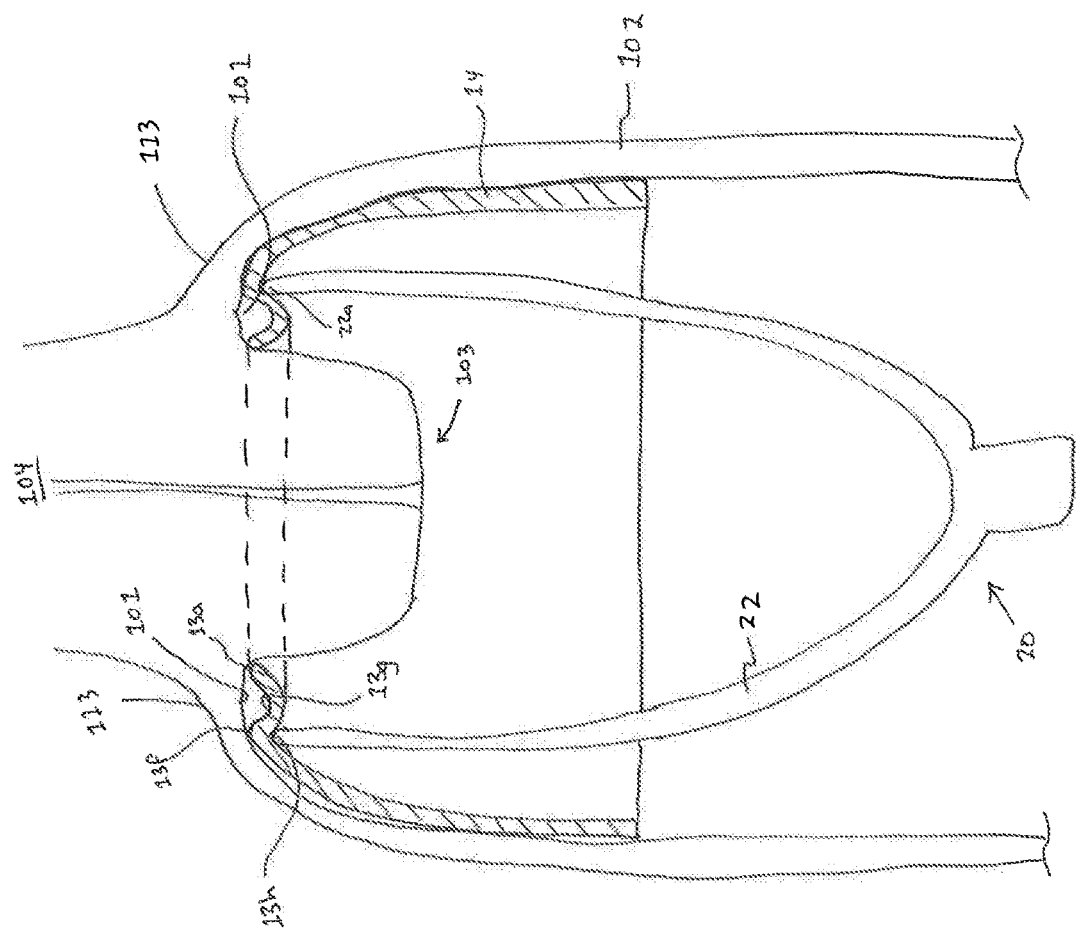

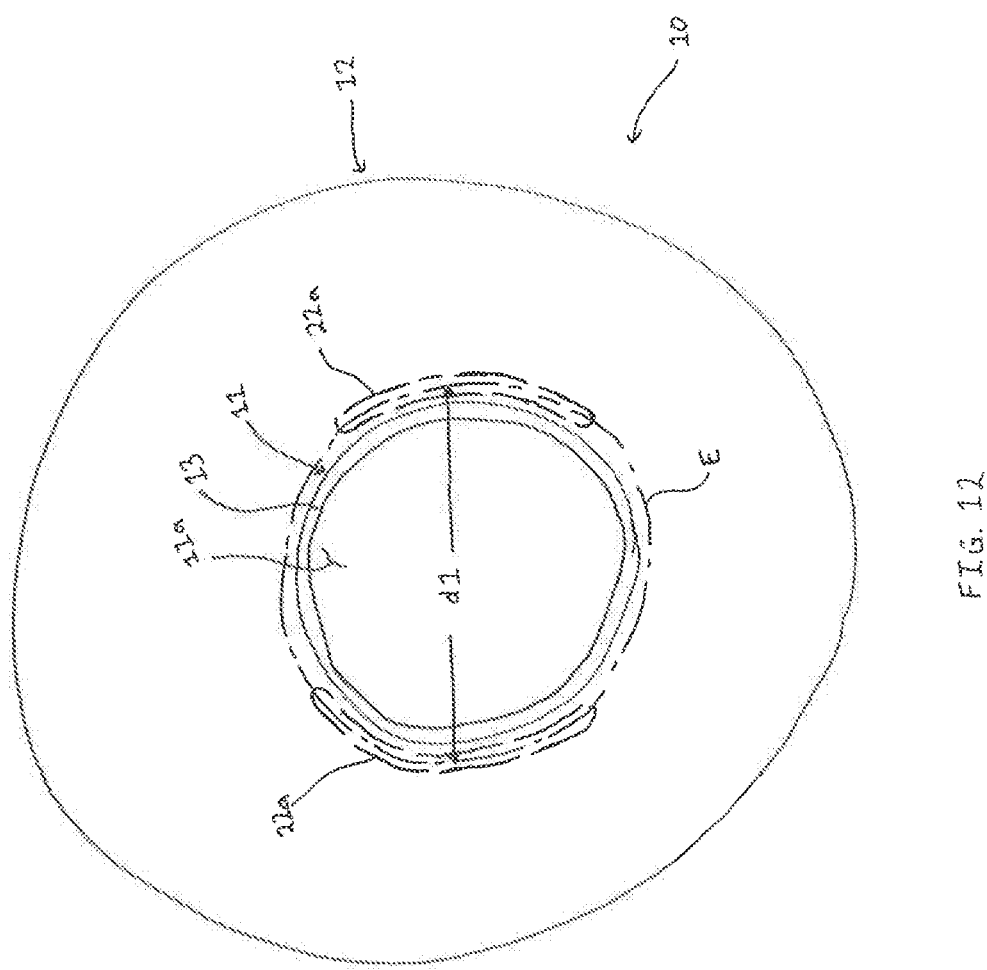

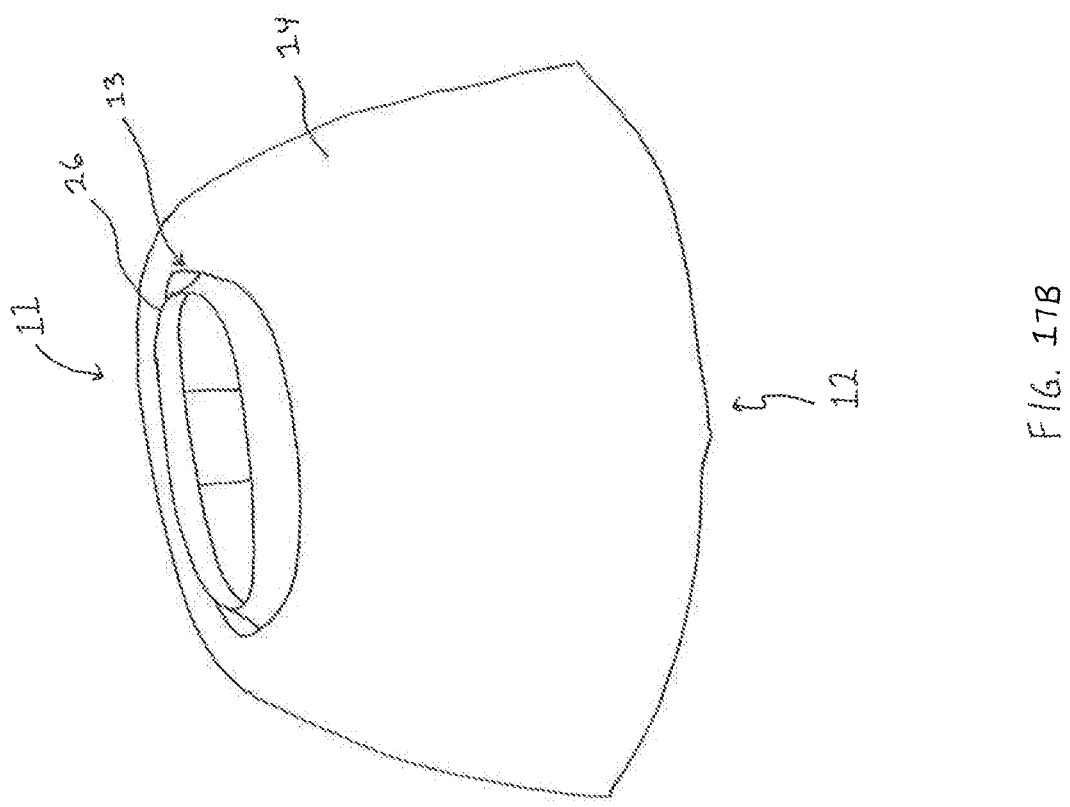
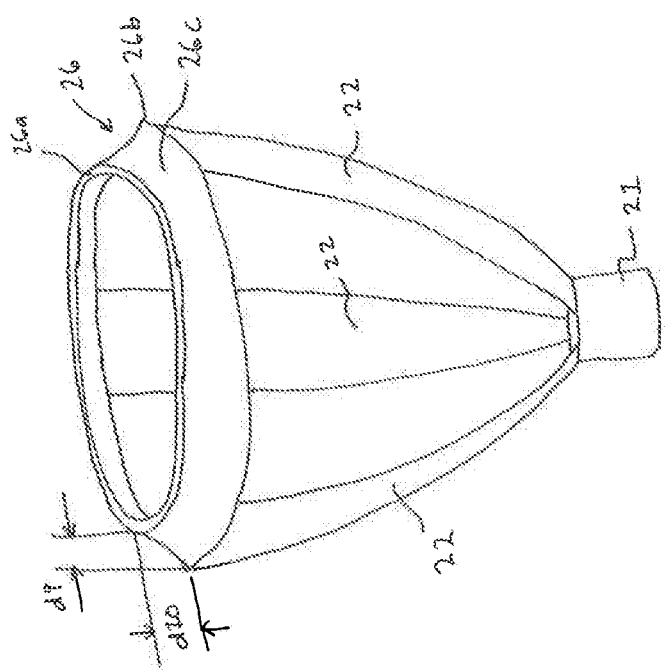

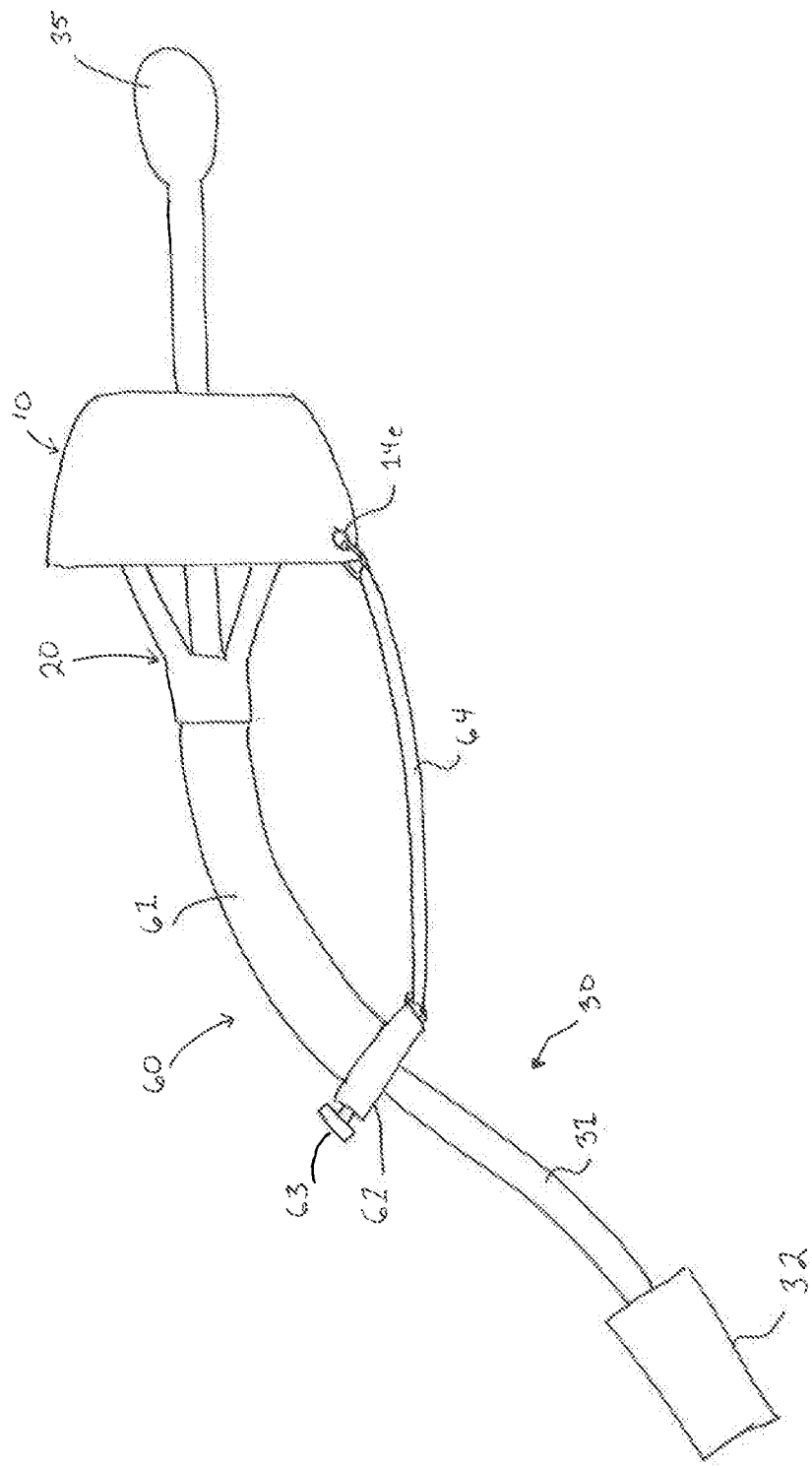

FORNIX MANIPULATOR

CROSS-REFERENCE TO RELATED APPLICATIONS

This U.S. non-provisional patent application claims priority under 35 U.S.C. § 119 of U.S. Provisional Application No. 61/326,326, filed on Apr. 21, 2010, the entire contents of which are hereby incorporated by reference.

BACKGROUND

1. Field of the Invention

The present disclosure relates to a fornix manipulator, and more particularly, to a device that delineates and deviates the vaginal fornix while preserving access to the cervix and supporting the vaginal wall to create a platform or plane for dissection.

2. Description of the Related Art

In some medical procedures, the vaginal fornix may need to be delineated and/or deviated away from other vital organs. In addition, the fornix and neighboring vaginal wall may need to be supported to provide a platform or plane for dissection. Many medical procedures require manipulation of the fornix. These include but are not limited to: hysterectomies; colpotomies; vaginal suspensions; colpoplexies; and resections of vesicovaginal fistulas, pelvic endometriesis, cancer, fibroids, and adhesions.

For example, in a hysterectomy, a surgeon cuts through the vaginal fornix to detach and remove the cervix and uterus from the body. Here, the vaginal fornix must be precisely delineated to prevent injury to the vaginal wall and neighboring vital organs, such as the bladder, bowel, or ureters. In addition to delineating the fornix, the surgeon may also have to deviate or move the fornix away from vital organs during incision. If organs are connected to the vaginal wall or fornix, the surgeon may also have to dissect or cut the connecting tissue. This requires supporting the fornix and vaginal wall together to provide an adequate platform or plane for dissection.

FIG. 1A-C illustrate the location of the fornix. FIG. 1A is a sagittal cross-section of a female pelvis. The cervix 103 opens into the uterus 104, and the ovaries 105 are connected to the uterus 104. On one side of the vagina 107, toward the front of the body, is a bladder 112 and a urethra 106 leading from the bladder to an outside of the body. On another side of the vagina 107, toward the rear of the body, is the rectum 109 between intestines 110 and the anus 108 which opens from the rectum 109 to outside the body.

FIG. 1B is a view of the cervix 103 from the vaginal canal. FIG. 1C is a simplified view of the uterus 104 from within the abdomen 111. Surgeons may access the uterus 104 and other organs from the abdominal cavity 111.

The fornix 100 is a cylindrical ring of tissue encircling the cervix 103 and lower uterus 104. The lowest cylindrical ring is the intra-vaginal fornix 101, The intra-vaginal fornix 101 encircles the cervix 103 and is visible from the vaginal canal, as illustrated by FIG. 1B. The intra-vaginal fornix 101 is located between the vaginal wall 102 and the cervix 103, as illiustrated by FIGS. 1A and 1B.

The upper-most cylindrical ring of the fornix 100 is the intra-abdominal fornix 113. When viewed from the abdomen, as in FIG. 1C, the anterior half of the intra-abdominal fornix 113 may be visible, but it is neither demarcated nor obvious to the human eye. It is therefore indicated with a dotted line. The ring of the intra-abdominal fornix 113 passes between the uterus 104 and rectum 104, and also passes between the uterus 109 and bladder 112, as indicated by FIG. 1.

The length of the fornix 100, or the distance between the lowest and upper-most cylindrical rings (i.e. the intra-vaginal fornix 101 and intra-abdominal fornix 113, respectively) is indicated by dotted lines in FIG. 1.

Several problems and injuries may result when using conventional devices, known as uterine manipulators, to manipulate the fornix 100. These problems include imprecise fornix delineation and deviation; vaginal shortening; and abdominal deflation. Injury can also result from blocked cervical access and blind cervical retrieval; device insertion and retrieval; and lack of a platform while dissecting vital organs away from the fornix and vaginal wall.

FIGS. 2A and 2B illustrate a first conventional device to perform uterine manipulation, and FIG. 3 illustrates a second conventional device. In the first conventional device 210, a first cup 211 has a first end 213 positioned at or near the intra-vaginal fornix 101. The second device 310 has a similar shape, with a single cup 311 having a first end 313 positioned at or near the intra-vaginal fornix 101. When pressure is applied against cups 211 or 311, their respective first ends 213 and 313 push the intra-vaginal fornix 101 against the intra-abdominal fornix 113. Eventually, the first end bulges through the fornix 100 into the abdomen as a distended ring of fornix tissue. The bulging ring formed by the first ends delineates the circumference of the fornix 100 when viewed from the abdomen.

Conventional devices may misestimate the location and diameter of the vaginal fornix 100, causing inaccurate delineation. The diameter of the first ends 213 and 313 of devices 210 and 310, respectively, may be greater than the diameter of the intra-vaginal fornix 101. Here, first ends 213 and 313 do not delineate the intra-vaginal fornix 101, but the upper third of the vaginal wall 102. In addition, the length of the cervix may be greater than the depths of the cups 211 and 311, respectively. Here, first ends 213 and 313 would not delineate the intra-vaginal fornix 101, since the length of the cervix 103 would prevent the ends 213 and 313 from reaching the intra-vaginal fornix 101. Rather, the devices would delineate the upper third of the vaginal wall.

When conventional devices misestimate the location and diameter of the vaginal fornix 100, the surgeon cannot precisely deviate the fornix away from other vital organs when operating inside the abdomen 111.

Inaccurate delineation can also lead to vaginal shortening. If a surgeon seeks to cut through the circumference of the fornix 100, the inaccurate delineation may cause the surgeon to cut through the vaginal wall 102, instead of in the fornix 100 itself. When a surgeon cuts the vaginal wall instead of the fornix 100, the length of the vaginal canal decreases.

Conventional uterine manipulators are also ill-suited for laparascopic and robotic surgeries that require abdominal inflation, also known as inflation of the peritoneal cavity. In laparoscopic and robotic surgeries, a camera and surgical tools are inserted through a navel port or small incisions on the lower abdomen. A constant supply of air or gas is pumped into the abdomen to inflate the abdomen. The inflated abdomen creates space for the surgeon to maneuver the camera and instruments without injuring vital organs. However, when a surgeon makes an incision through the vaginal fornix, gas escapes from the abdomen through the vaginal canal. When the air leaks out, the abdomen disinflates, making it difficult to maneuver instruments and increasing the risk of organ injury.

Conventional uterine manipulators do not prevent abdominal disinflation. Rather, incised tissue retracts from the point of the incision and creates a hole or space between the device and tissue for air to escape. In the first device 210, since the first end 213 of the first cup 211 has a diameter greater than the second end 214, the tissue of the vaginal wall 102 retracts from the incision at the first end 213 toward the second end 214. A space forms between the vaginal wall 102 and first device 210. Consequently, air escapes from the abdominal cavity 111. The second device 310 attempts to prevent air leakage by inflating a balloon 312 within the vagina 107. However, air may continue to leak, and at the same time, the cervix 103 cannot be accessed from the vagina 107.

Conventional uterine manipulators block access to the cervix from the vagina 107. For example, the first device 210 blocks access to the cervix 103 with both the first and second cups 211 and 212, and the second device 310 blocks access to the cervix 103 with the balloon 312. Consequently, if the cervix 103 and attached uterus 104 must be retrieved from the vagina 107 after a hysterectomy, the surgeon must first remove the uterine manipulator and then reach into the vagina 107 to blindly feel around for the cervix 103. At times, the surgeon pulls and tears the incised fornix 100 or vaginal wall 102. In robotic operations in particular, this may add significant time to the procedure, since it requires the surgeon to scrub before reaching in.

Conventional uterine manipulators pose injury risks in removal. For example, the cups 211, 212, and 311 may get stuck in the vaginal canal when the uterine manipulator 230 or 330 is extracted from the vagina 107. This may occur since the diameter of the cups may be larger than a diameter of the vaginal opening. To retrieve the cups, the surgeons must blindly reach and fish for the cups. At times, the surgeon may pull and damage tissue, or the surgeon may have cut the vaginal opening to remove the cups.

Conventional uterine manipulators also pose injury risks upon insertion. Since the devices are of predetermined diameters with the first end larger than the second end, the tissue of the vaginal wall 102 may be damaged when the vagina 107 has a smaller diameter than the diameters of the first ends of devices 210 and 310.

Conventional uterine manipulators do not provide a platform or plane for dissection. For example, when performing a hysterectomy, the surgeon may need to dissect vital organs such as the bladder 112 and the rectum 109 away from the vaginal wall. These vital organs are connected to the vaginal wall 102 and at times the fornix 100. Thus, heat from cauterizing the fornix 100 may travel through the tissue and injure the these organs if not dissected away. In the first device 210, cups 211 and 212 become narrower at their intersection 210, and therefore do not provide a surface or plane on which to perform a dissection. The second device 310 likewise does not provide a surface for dissection since there are spaces or holes in cup 312. The lack of a platform or even plane increases the risk of injury to vital organs in hysterectomies as well as other operations that require resections, such as operations to remove endometriosis, cancer, fibroids, pelvic adhesions, and vesicovaginal fistulas.

SUMMARY

The present general inventive concept relates to a fornix manipulator which includes a collar and a stabilizer. The fornix manipulator addresses the above-described problems, including imprecise fornix delineation and deviation; vaginal shortening; abdominal deflation; blocked cervical access; and unnecessary tissue damage from blind cervical retrieval, device insertion and retrieval, and lack of a platform for organ dissection. However, the present general inventive concept is not limited to addressing only the above-described problems, and other benefits, features, and/or utilities of the present general inventive concept may be apparent to one of ordinary skill in the art.

Features of the present general inventive concept may be realized by a collar having a first end and a second end having a diameter greater than the first end, the first end having a first opening to receive a cervix into the collar and a rim to encircle the opening, and the second end having a second opening, the collar having an inner surface and outer surface, wherein the outer surface is in contact with the vaginal wall, and a stabilizer comprising a base portion and a plurality of prongs extending from the base portion into the second end of the collar, wherein the ends of the prongs contact the collar.

The ends of the prongs may contact an inner surface of the first end of the collar.

The collar may have one of a trapezoid cross-section shape, a domed cross-section shape, or a combination of a trapezoid and domed cross-section shape.

The collar may have a plurality of parallel ridges around an outer surface of the collar.

The collar may have one of a hole, ring, tab, or other protrusion fixed to the collar to receive a strap.

The rim may include an outer edge, an inner edge, and a rim surface between the outer edge and the inner edge to define the opening, and the rim surface is angled with respect to a plane defined by the outer edge.

The rim may include a protrusion extending inward toward a middle portion of the collar from the first end.

The collar rim may include a first outer rim edge adjacent to the first opening and a second outer rim edge separated from the first outer rim edge by a gully.

The ends of the prongs may contact a trough on the inner surface between the second outer rim edge and collar wall.

The base portion of the stabilizer may have a guide hole.

The ends of the prongs of the stabilizer may contact a rim on the inner surface of the first end of the collar.

The stabilizer may include a stabilizer rim connecting the ends of the prongs that are opposite the base portion.

The stabilizer rim may contact an inner surface of the first end.

The stabilizer rim may contact a rim on the inner surface of the first end.

The stabilizer rim may contact a trough on the inner surface between the second outer rim edge and collar wall.

The stabilizer rim may include an outer edge, an inner edge, and a rim surface between the outer edge and the inner edge to define the opening, and the rim surface is angled with respect to a plane defined by the outer edge.

The stabilizer rim may include an inner edge, an outer edge that is closer than the inner edge to the base portion in a linear direction and farther from a center of the stabilizer in a radial direction than the inner edge, and an outer rim surface that connects the inner edge to the outer edge.

A diameter of the inner edge of the stabilizer rim is smaller than a diameter of the collar rim, such that a gap is located between the inner edge of the stabilizer rim and the collar rim when the outer edge of the stabilizer is in contact with the inner surface of the first end of the collar.

The inner edge of the stabilizer rim may extend past the collar rim in a linear direction when the outer edge of the stabilizer is in contact with the inner surface of the first end of the collar.

The inner edge of the stabilizer rim may be flush with the collar rim when the outer edge of the stabilizer is in contact with the inner surface of the first end of the collar.

Features of the present general inventive concept may also be realized by a collar, including a first end including a rim to define a first opening, the first end having a first diameter, a second end having a second opening and having a second diameter greater than the first diameter, and a side wall between the first end and the second end to define an inner cavity between the first opening and the second opening, wherein the first diameter is such that a cervix of a predetermined second diameter slides into the first opening and is located in the cavity.

The rim of the first end may circumscribe a vaginal fornix.

The collar may have one of a trapezoid cross-section shape, a domed cross-section shape, or a combination of a trapezoid and domed cross-section shape.

The collar may include a plurality of parallel ridges located around an outside surface of the side wall.

The collar may have one of a hole, ring, tab, or other protrusion fixed to the collar to receive a strap.

The rim may include a first outer rim edge adjacent to the first opening and a second outer rim edge separated from the first outer rim by a gully.

The rim may include a protrusion extending inward toward the inner cavity from the first end.

The rim may include an outer edge, an inner edge, and a rim surface between the outer edge and the inner edge to define the opening, and the rim surface is angled with respect to a plane defined by the outer edge.

The rim surface may have one of a concave and a convex shape.

Features of the present general inventive concept may also be realized by a stabilizer to contact one of a rim or ring encircling a cervix, the stabilizer including a plurality of prongs extending from a base portion to contact the one of a rim or ring.

The stabilizer of embodiments, wherein the base portion has a guide hole.

The ends of the prongs may include one of a protrusion and a notch to latch a respective notch or protrusion of one of a rim or ring to connect to the rim or ring.

The ends of the plurality of prongs opposite the base portion may be connected by a rim.

The stabilizer rim may have a surface to contact a surface of one of a rim or ring.

The stabilizer rim may include an outer edge, an inner edge, and a rim surface between the outer edge and the inner edge to define the opening, and the rim surface is angled with respect to a plane defined by the outer edge.

The rim surface may be one of a concave or convex shape.

The stabilizer rim may include an inner edge, an outer edge that is closer than the inner edge to the base portion in a linear direction and farther from a center of the stabilizer than the inner edge in a radial direction, and an outer rim surface that connects the inner edge to the outer edge.

The outer rim surface may be concave-shaped.

The prongs may extend from the base portion to form one of a "U" shape, a "V" shape, or a wishbone shape, with the base portion located at a center point of the "U," the "V", and the wishbone, respectively.

Ends of the plurality of prongs opposite the base portion may not be mechanically connected to each other.

BRIEF DESCRIPTION OF THE DRAWINGS

The accompanying drawings are included to provide a further understanding of the general inventive concept and are incorporated in and constitute a part of this specification. The drawings illustrate exemplary embodiments of the general inventive concept and, together with the description, serve to explain principles of the general inventive concept.

FIG. 1A illustrates a sagittal cross-section of a female pelvis. FIG. 1B is a view of the cervix 103 from the vaginal canal. FIG. 1C is a view of the uterus 104 from within the abdomen 111.

FIGS. 2A and 2B illustrate an example of a conventional device used to perform operations and procedures relating to the vaginal fornix.

FIG. 4 illustrates placement of a fornix manipulator within a vaginal canal.

FIGS. 8A to 8F illustrate views of a collar according to an embodiment of the general inventive concept including a gully or trough between an outer rim and an inner rim.

FIGS. 9A to 9C illustrate varied shapes of the prongs in relation to the base of the fornix manipulator.

FIGS. 11A to 11C illustrate operation of the stabilizer and the collar according to embodiments of the general inventive concept.

FIG. 12 illustrates a shape of the end portions of the stabilizer's prongs.

FIGS. 17A to 17D illustrate a stabilizer according to another embodiment of the present general inventive concept having a protruding rim.

FIG. 19 illustrates a fornix manipulator when used in conjunction with to a uterine shaft device.

DETAILED DESCRIPTION OF THE EMBODIMENTS

Figure 1B:
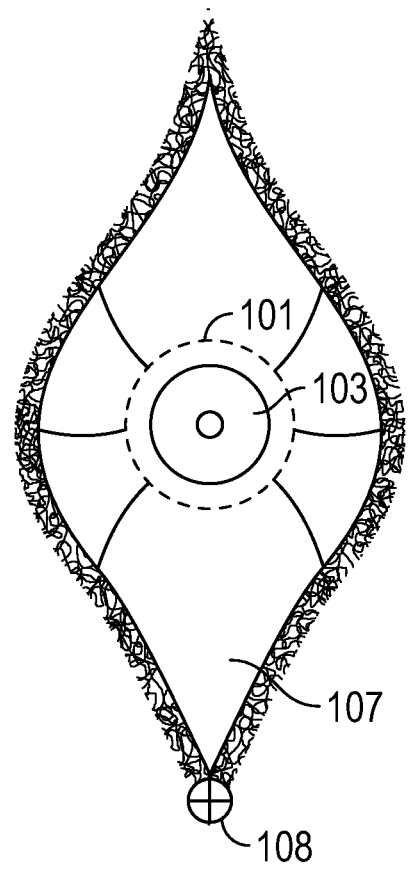
FIGS. 1A-C illustrate a basic anatomy around the cervix, uterus, and vagina.
Figure 1:
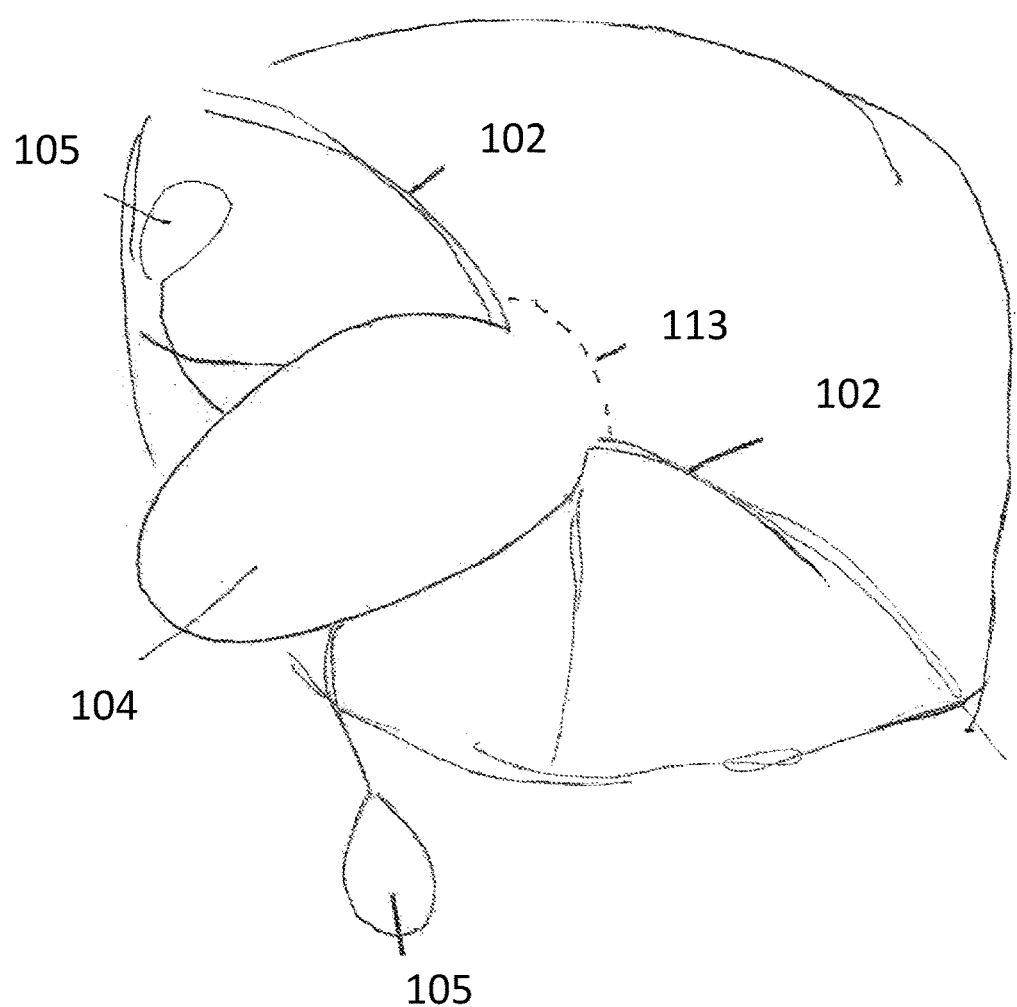

Preferred embodiments of the general inventive concept will be described below in more detail with reference to the accompanying drawings. The embodiments of the general inventive concept may, however, be embodied in different forms and should not be constructed as limited to the embodiments set forth herein. Rather, these embodiments are provided so that this disclosure will be thorough and complete, and will fully convey the scope of the general inventive concept to those skilled in the art. Like numbers refer to like elements throughout.

FIG. 4 illustrates a fornix manipulator composed of a collar 10 and a collar stabilizer 20 in operation inside a vaginal canal. The collar 10 and the stabilizer 20 may slide onto a uterine shaft 30 and be inserted into the vagina 107. A contact end of the collar 10 may slide over the cervix 103 and be pressed in contact with the intra-vaginal fornix 101 surrounding the cervix 103. Pressure against the stabilizer 20 causes the contact end of the collar 10 to further press against the intra-vaginal fornix 101, causing the fornix 100 to distend into the abdomen and producing a bulge visible on the intra-abdominal fornix 113. This bulge delineates the fornix 100 for incision. A uterine shaft locking screw may lock the stabilizer in place to maintain pressure against the intra-vaginal fornix 101 and preserve delineation. An incision may be made in the abdomen and medical instruments, such as scalpels, cameras, or any other medical instruments may be introduced into the abdominal cavity 111. The fornix 100 may be incised by cutting the delineating bulge on the distended intra-abdominal fornix 113. The fornix 100 may also be deviated by moving the shaft attached to the stabilizer 20 and collar 10. In addition, the dome wall 14 of the collar 10 may provide a platform for dissection of vital organs and tissue from the vaginal wall 102. Additionally, at least one or more windows 400 is formed between a plurality of progs and between the stabilizer rim and the base portion of the stabilizer.

Operation of the collar 10 with respect to the cervix 103, vaginal fornix 100, and other tissues will be described in greater detail below.

Figure 2A:
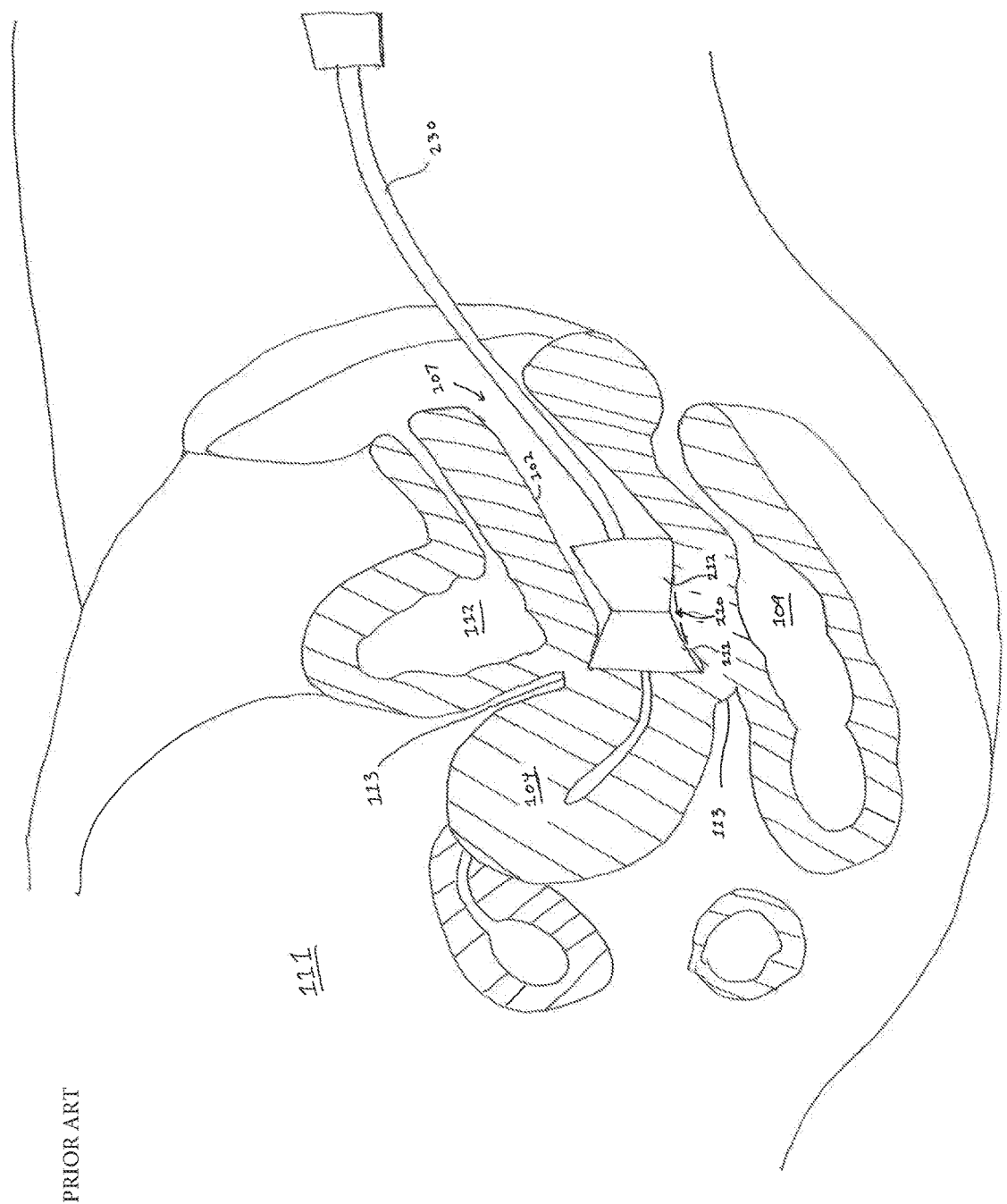
Figure 3:
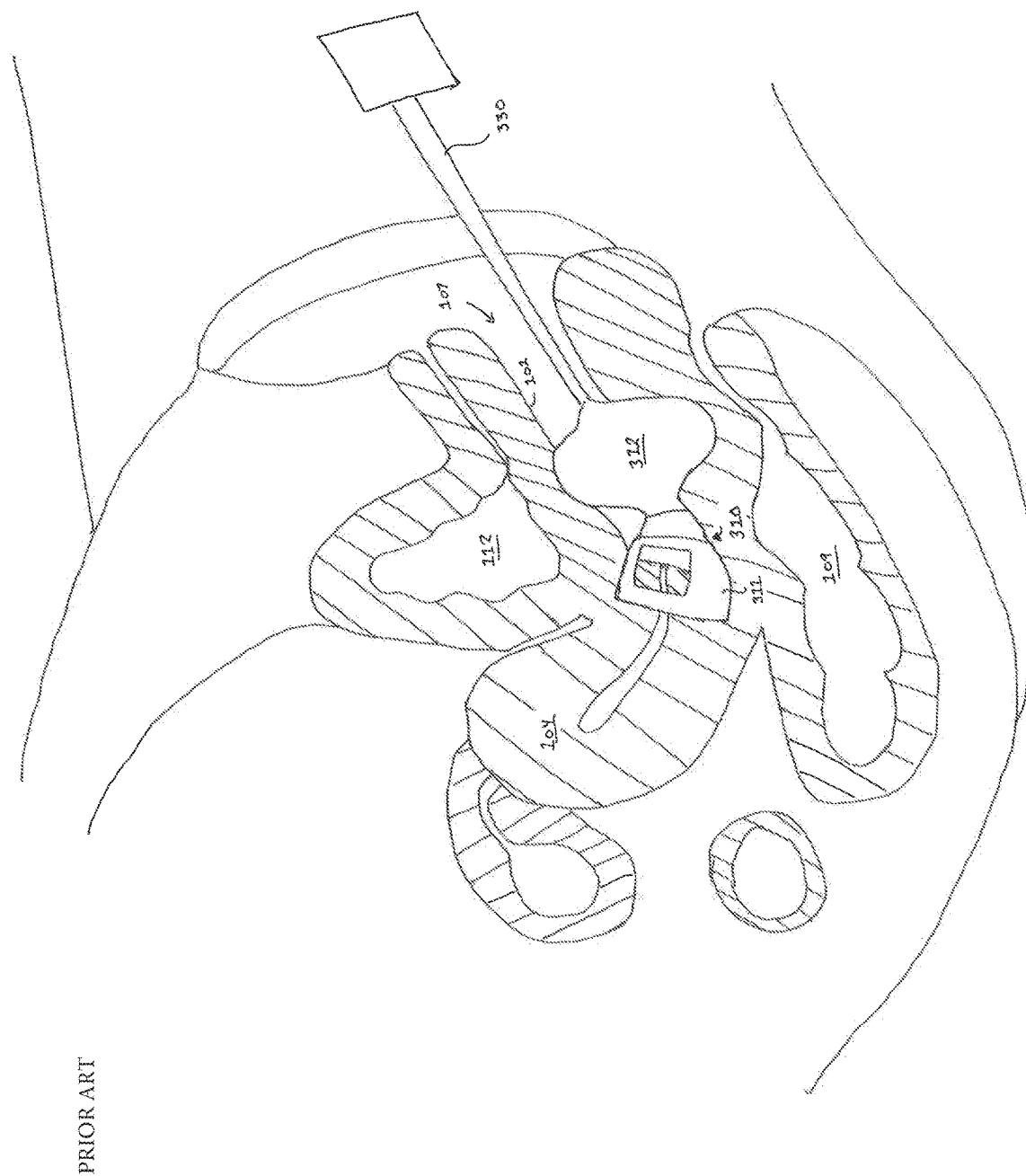
FIG. 3 illustrates another example of a conventional device used to perform operations and procedures relating to the vaginal fornix.
Figure 5B:
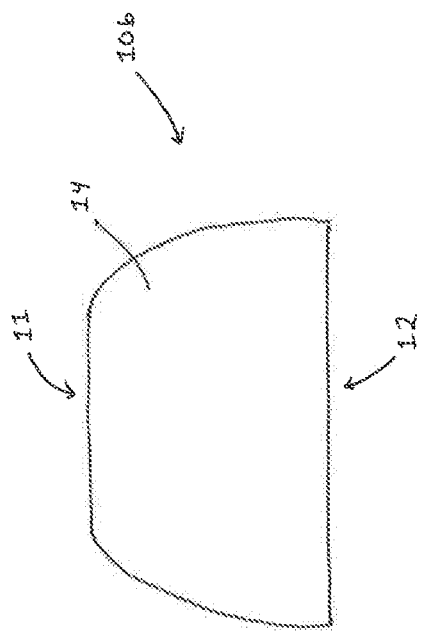
FIGS. 5A and 5B illustrate shapes of the fornix manipulator's collar.
Figure 5A:
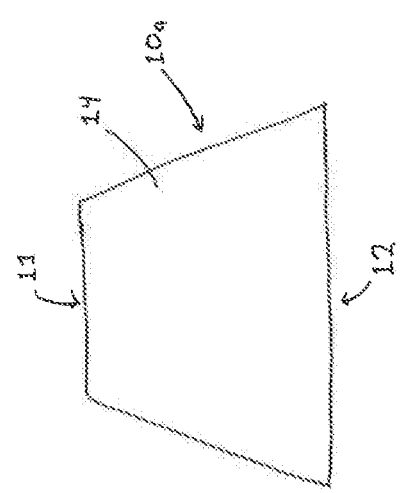

FIGS. 5A and 5B illustrate a shape of the collar 10 according to embodiments of the general inventive concept. As illustrated in FIG. 5A, the collar 10a includes a contact end 11 and a receiving end 12. A side wall 14 defines a profile of the collar 10a. The collar 10 may have a trapezoidal profile, as illustrated in FIG. 2A, a dome-shaped profile, as illustrated by the collar 10b of FIG. 2B, or any other appropriate shape to define and support the vaginal wall. For example, the side walls 14 may have a straight line shape, a convex shape, or any combination of the two shapes. Side wall 14 expands the vaginal canal and provides a platform or plane for dissecting vital organs away from the vaginal wall 102. Organs such as the bladder, ureters, rectum and bowel are protected from heat produced by cauterization of the fornix 100. This is particularly important in procedures such as hysterectomies; colpotomies; vaginal suspensions; colpoplexies; and resections of vesicovaginal fistulas, pelvic endometriesis, cancer, fibroids, and adhesions.

In addition to providing a platform for dissection, the dome or trapezoidal shape of the collar is critical to solving the problem of abdominal disinflation. The increasing diameter of the collar 10 makes it difficult for the tissue to retract from the contact end 11 to the receiving end 12. In conventional devices, the diameter decreases, allowing the tissue to retract back easily since the diameter of the incision exceeds the diameter of the cup edge used to delineate the incision.

In addition, the increasing diameter of the collar 10 minimizes the risk of vaginal injury upon insertion of the device to the vaginal canal. In contrast to conventional devices that insert largest diameter end first, the fornix manipulator inserts the smallest diameter end first, thereby allowing the vaginal opening to expand to the larger diameter as the device is inserted.

The collar 10 may be made of semi-rigid or rigid material that does not change in shape in response to a force from the stabilizer 20 or any other device. This allows the collar 10 to serve as an adequate platform for dissection and allows it to delineate the fornix 100 with precision. However, the material may be semi-rigid to allow compression of the outer end 12 when removing the device from the vaginal canal after the medical procedure.

Figure 6B:
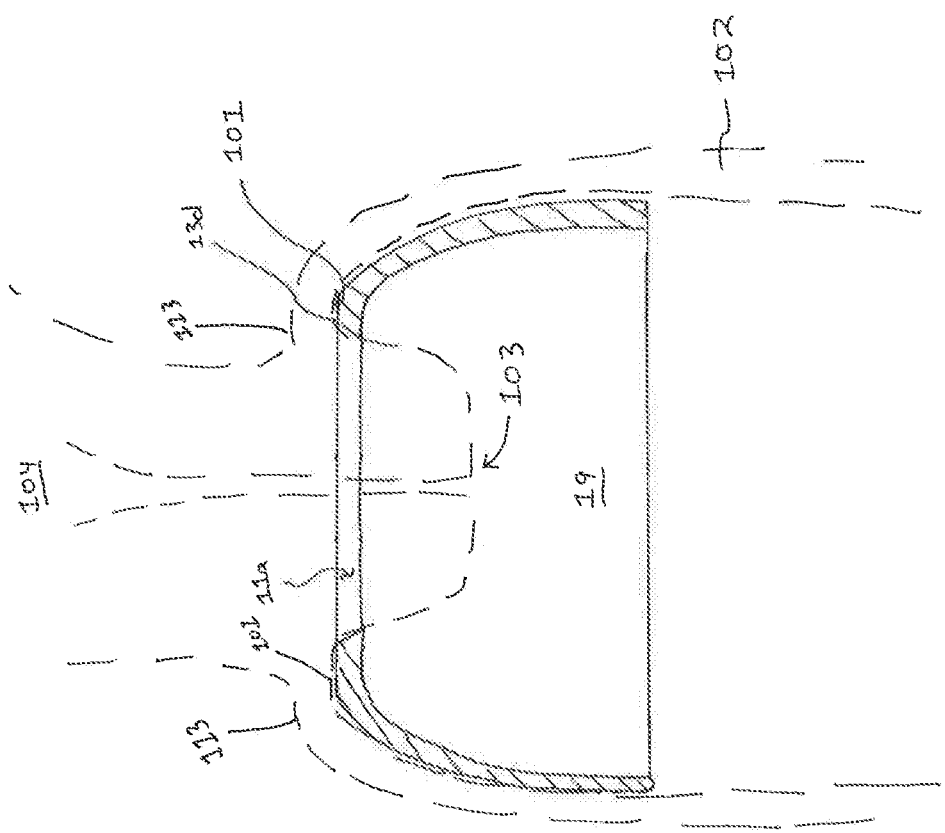
FIGS. 6A to 6D illustrate cross-section views of the collar.
Figure 6A:
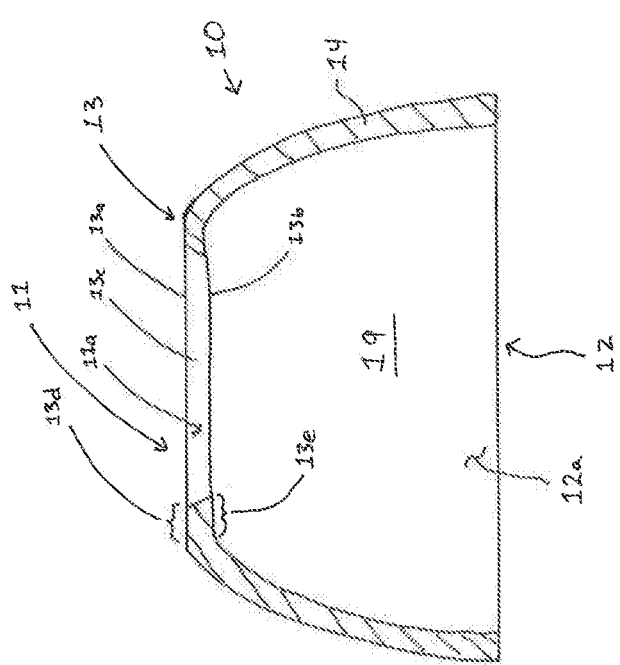

FIG. 6A illustrates a cross-section view of the collar 10 according to an embodiment of the present general inventive concept. The side wall 14 of the collar 10 defines an opening 11a of the contact end 11 and another opening 12a in the receiving end 12. The side wall 14 may define a cavity or hollow tunnel 19 between the openings 11a and 12a. The opening 11a may be defined by a rim 13 having an outer edge 13a, an inner edge 13b, and a rim surface 13c between the outer and inner edges 13a and 13b. The outer surface of the rim 13 may define an outer rim surface 13d surrounding the opening 11a. The inner surface of the rim 13 opposite the outer rim surface 13d may define an inner rim surface 13e. The rim surface 13c may be formed at an angle with respect to a plane defined by the outer edge 13a or the outer rim surface 13d.

Figure 6D:
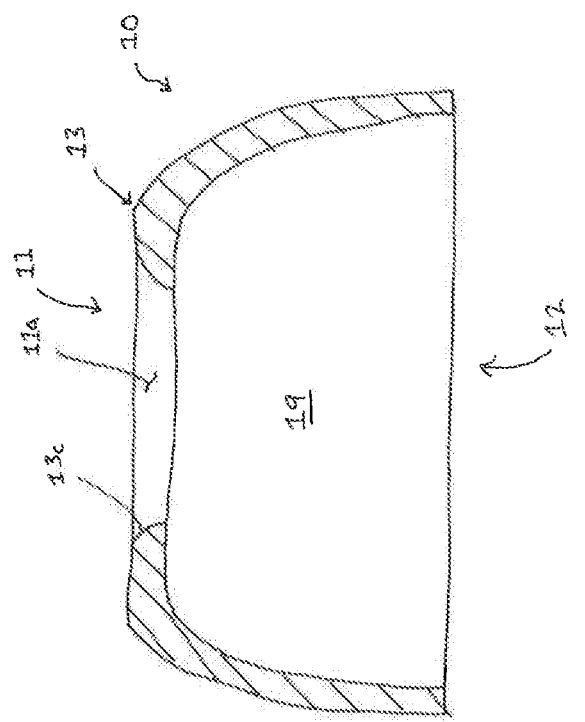
Figure 6C:
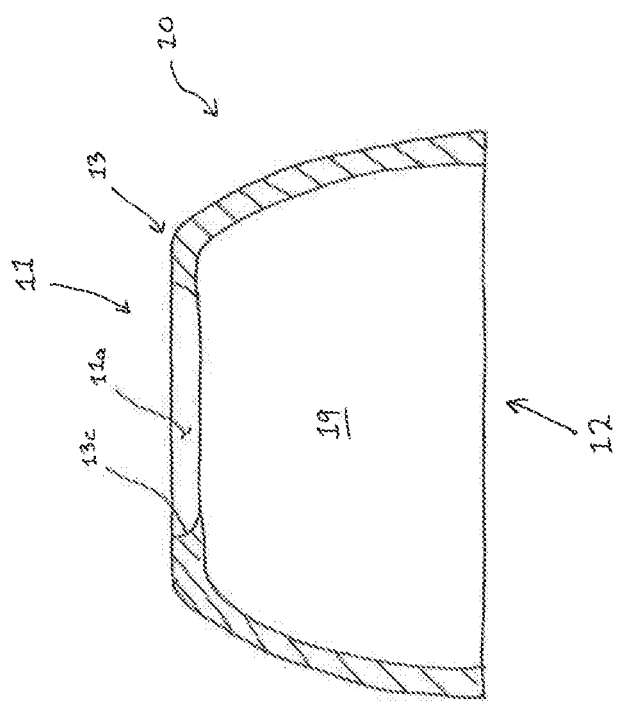

As illustrated in FIG. 6A, the rim surface 13c may have a substantially flat or planar surface. FIGS. 6C and 6D illustrate alternative embodiments of the rim surface 13c. In FIG. 6C, the rim surface 13c has a concave shape, so that a center portion of the rim surface 13c is curved inward with respect to the outer rim 13a and the inner rim 13b. FIG. 6D illustrates a rim surface 13c having a convex shape, so that the center portion of the rim surface 13c is curved outward with respect to the outer rim 13a and the inner rim 13b.

FIG. 6B illustrates the placement of the collar 10 (which includes a hollow tunnel 19) with respect to the cervix 103. The rim 13 of the collar 10 may be placed around the outside of the cervix 103, so that the outer rim surface 13d contacts the tissue surrounding the cervix 103, including the intra-vaginal fornix 101. The cervix 103 may be guided into the opening 11a by the angled rim surface 13c.

The open receiving end 12 of the present general inventive concept allows the collar 10 to delineate the fornix 101 for a cervix 103 of any length, even when the cervix 103 extends to or past the receiving end 12. Conventional devices have closed ends corresponding to the receiving end 12, As a result, when the length of the cervix 103 is greater than the depths of their respective cups 211 and 311, the cervix prevents the respective ends 213 and 313 from reaching the intra-vaginal fornix 101. If an incision is made around the edges of the misestimating cups, vaginal shortening results. In other words, the conventional device may delineate a portion of the vaginal wall 102, instead of the fornix 100. Here, however, the collar 10 of the fornix manipulator may slide up the cervix 103 to the intra-vaginal fornix 101. An abnormally long cervix will simply abut from the second opening 12a. Thus, because the rim 13 of the collar precisely locates the intra-vaginal fornix 101, there is no vaginal shortening when a surgeon seeks to incise the fornix 100.

Because the collar has two openings, instead of one, and because the diameter of the first opening of the collar is measured to fit the diameter of the cervix, the fornix is precisely delineated and deviated. As a result, there is no vaginal shortening. The collar 10 may be chosen from among a plurality of collars 10 having various sizes to suit the particular patient. The intra-vaginal fornix 101 of the patient may be measured in advance of an operation, and a collar 10 having a rim 13 corresponding to the measured size of the intra-vaginal fornix 101 or a diameter corresponding to the diameter of the cervix may be used in the operation. As a result, the rim 13 of the collar 10 is always in contact with the fornix, as opposed to the vaginal wall. The precise delineation prevents the surgeon from cutting into the vaginal wall, thereby preventing any vaginal shortening.

Figure 7B:
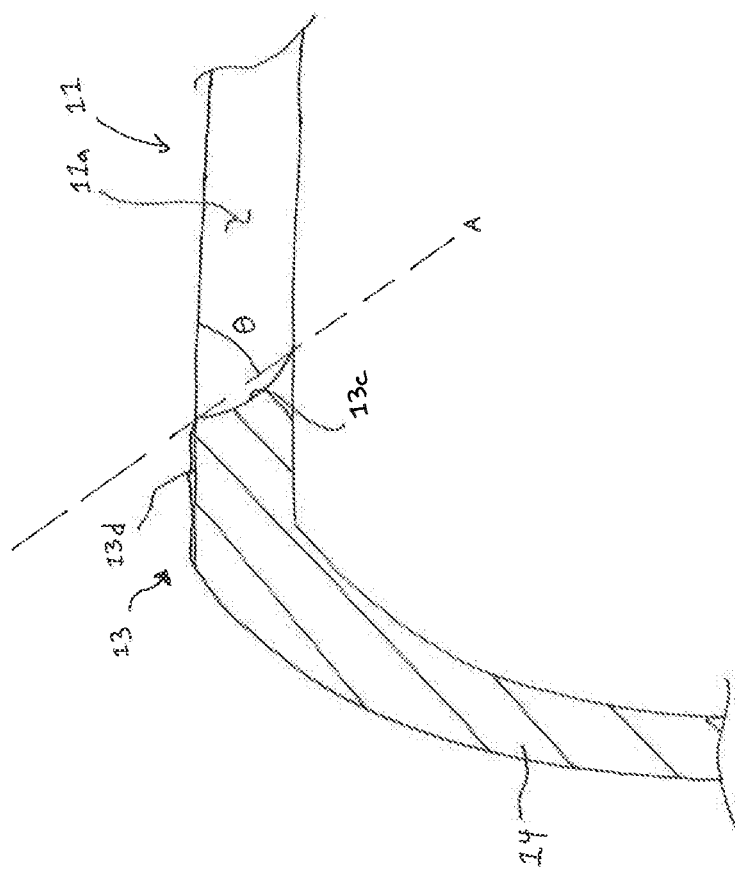
FIGS. 7A to 7C illustrate an angle of the rim of the collar or, alternatively, (if a rim connects the prongs of a stabilizer), the rim of a stabilizer.
Figure 7A:
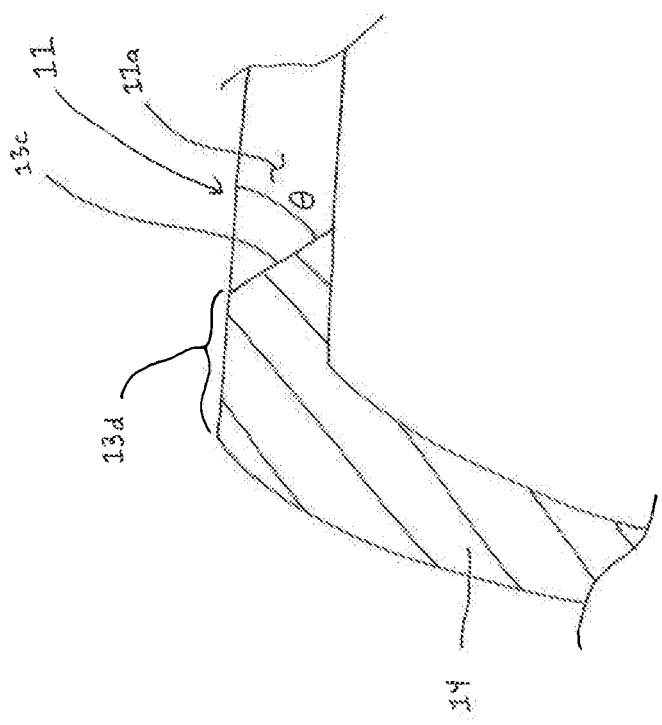
Figure 7C:
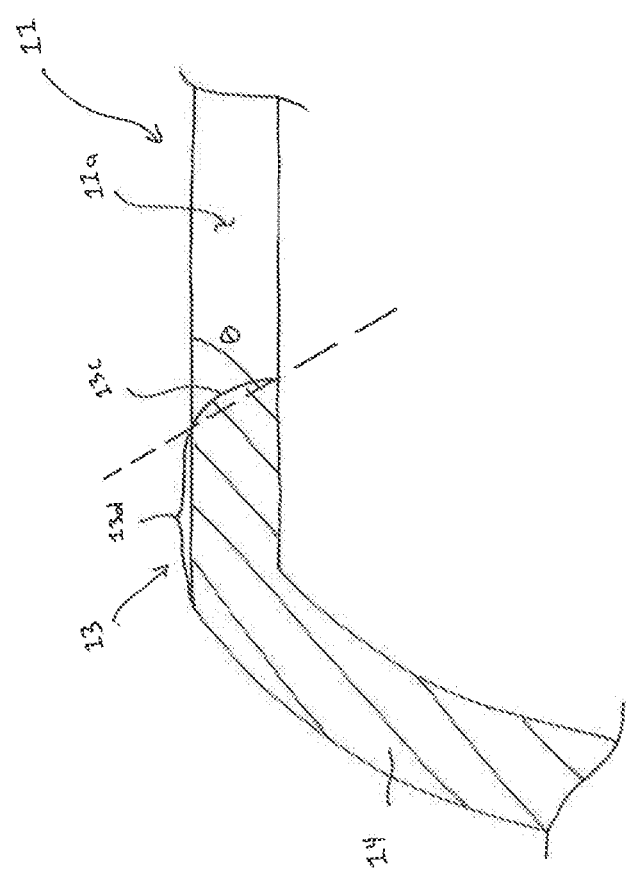

FIGS. 7A to 7C illustrate the angle of the rim surface 13c with respect to a plane defined by the outer rim surface 13d of the contact end 11. As illustrated in FIG. 7A, when the rim surface 13c has a substantially flat surface, the entire rim surface 13c may be angled with respect to the outer rim surface 13d at a constant angle. In other words, since the outer rim surface 13d surrounds the opening 11a to form a substantially planar disc shape along a plane, at any given point along a cross-section of the rim surface 13c, a line passing through substantially any two points of the rim surface 13c will be angled at an angle θ with respect to the plane defined by the outer rim surface 13d.

In FIG. 7B, when the rim surface 13c has a concave shape, a line A passing through the ends of the rim surface 13c may form an angle θ with respect to a plane defined by the outer rim surface 13d. Similarly, as illustrated in FIG. 7C, when the rim surface 13c has a convex shape, a line B passing through the ends of the rim surface 13c may form an angle θ with respect to the plane defined by the outer rim surface 13d.

The angle θ may be any desired angle. For example, the angle θ may be between 20 degrees and 70 degrees.

When a stabilizer contains a rim surface connecting the prongs, as will be later discussed (e.g., rim surface 25, FIG. 14B; rim surface 26a, FIG. 17A), the stabilizer's rim surface may similarly have an angle as illustrated in FIGS. 7A to 7C.

Figure 8B:
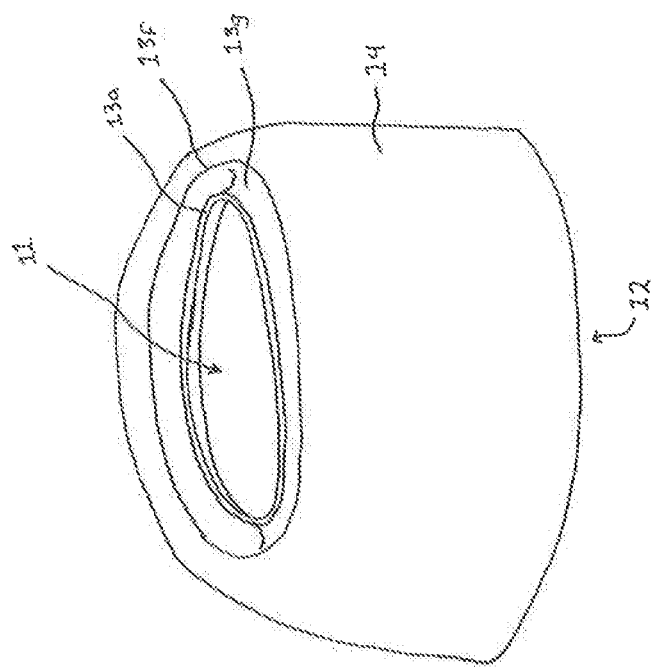
Figure 8A:
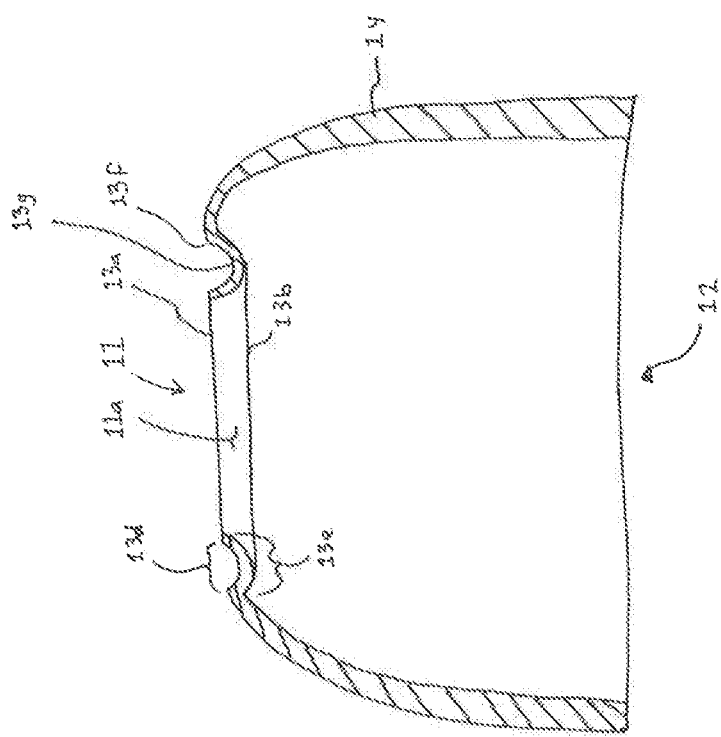

FIGS. 8A to 8C illustrate the collar 10 or collar according to another embodiment of the present general inventive concept. The collar 10 may include a first outer rim edge 13a and a second outer rim edge 13f separated by a trough or gully 13g. According to the embodiment illustrated in FIGS. 8A to 8C, the intra-abdominal fornix 113 may be located in the vicinity of the trough 13g, so that as a surgeon probes the distended intra-abdominal fornix 113 from the abdominal cavity 111, the surgeon can precisely find the location of the intra-abdominal fornix 113 by probing for the trough 13g between the ridges of outer rim edges 13a and 13g.

Figure 8E:
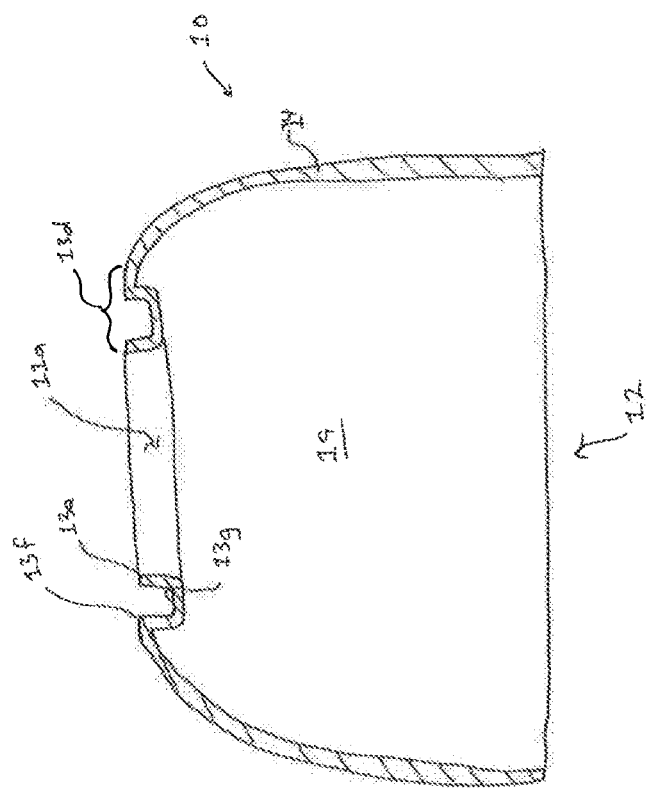
Figure 8D:
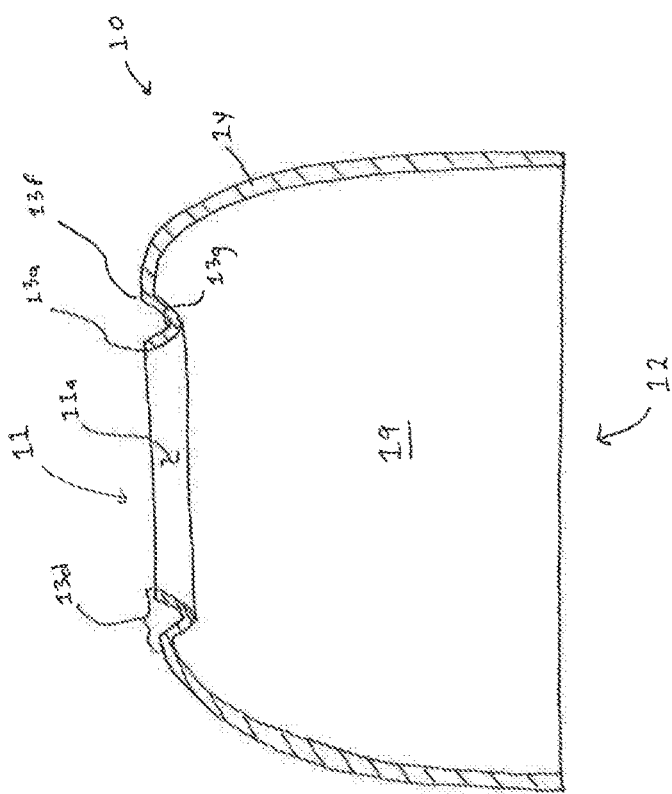

The second outer rim edge 13f may be flush with a plane defined by the first outer rim edge 13a, may protrude past an end of the plane defined by the first outer rim edge 13a, or may be recessed back from the plane defined by the first outer rim edge 13a. The first and second outer rim edges 13a and 13f may have rounded or angular shapes. Similarly, the trough 13g may have a rounded shape or angular shape. For example, as illustrated in FIGS. 8D and 8E, the trough 13g could have a shape of a reversed triangle, having one point in the nadir of the trough, or of a rectangle, having one side at the nadir of the trough.

When the rim 13 includes first and second outer rim edges 13a and 13f, as illustrated in FIGS. 8A to 8E, the surface of the rim 13 defining the opening 11a may have the angled shape, as described above with respect to FIGS. 7A to 7C. For example, FIG. 8F illustrates a collar 10 having a rim 13 with both first and second outer rim edges 13a and 13f, and an angled rim surface 13a with respect to a plane defined by the outer rim surface 13d.

FIGS. 9A to 9C illustrate a stabilizer 20 according to embodiments of the present general inventive concept. The stabilizer 20 includes a base portion 21 and prongs 22. Prongs 22 include first ends couple to base portion 21 and free ends extending from the base portion 21. The base portion 21 includes walls 23 that define an opening 24 at a center portion of the base portion. The opening 24 may be of sufficient size to pass a tube or shaft, such as the shaft of the uterine manipulator 30 of FIG. 4. As illustrated in FIGS. 9A to 9C, the stabilizer 20 may have a "V" shape similar to the stabilizer 20a of FIG. 9A, a "U" shape similar to the stabilizer 20b of FIG. 9B, a wishbone shape similar to the stabilizer 20c of FIG. 9C, or any other appropriate shape.

Figure 10C:
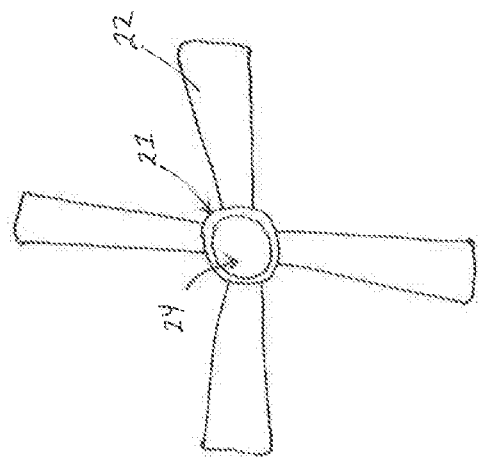
FIGS. 10A to 10C illustrate varied configurations of prongs of the fornix manipulator.
Figure 10B:
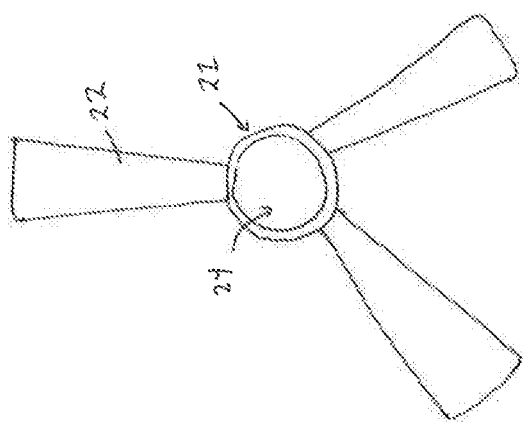
Figure 10A:
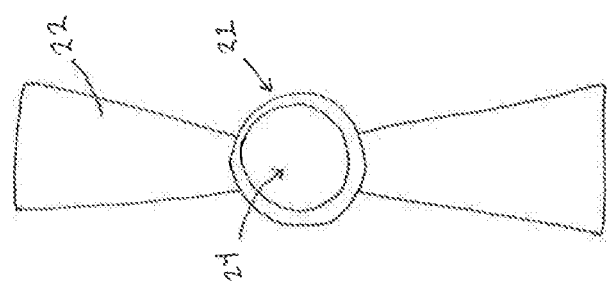

FIGS. 10A to 10C illustrate views of the stabilizer 20 as seen from the base 21. The stabilizer 20 may have any desired number of prongs, including two prongs (FIG. 10A), three prongs (FIG. 10B), or four prongs (FIG. 10C), or more than four prongs.

Figure 13B:
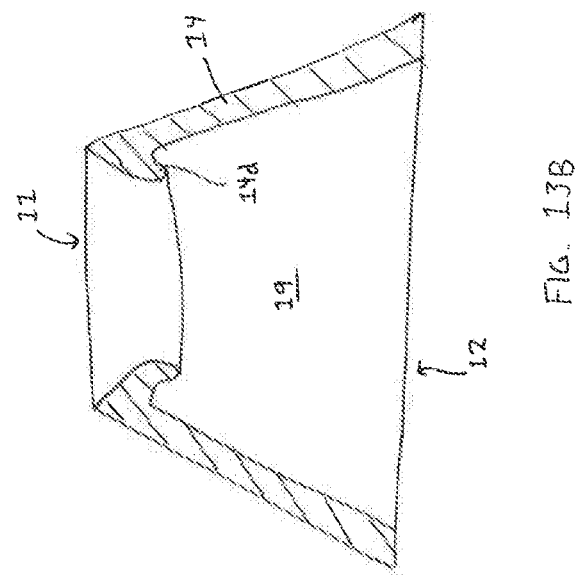
FIGS. 13A to 13D illustrate inner ridges of the collar.

FIGS. 11A and 11B illustrate the stabilizer 20 in connection with the collar 10. As illustrated in FIG. 11A, the prongs 22 of the stabilizer 20 may be positioned within the collar 10. More particularly, the ends 22a of the prongs 22 may be positioned against the inside rim surface 13e of the collar 10. The ends 22a may be connected to the collar 10 via adhesive, welding, or any other method. Alternatively, the ends 22a may snap into the side walls, as illustrated in FIG. 13B-13D. According to yet another alternative, the ends 22a may be held in place against the inside rim surface 13e of the collar 10 only by a pressing force. That is, the stabilizer 20 and collar 10 may be separate pieces. Like the collar, the stabilizer 20 is semi-rigid or rigid so it may maintain a pressing force against the inside rim surface 13e of the collar 10 while being compressable for removal.

The stabilizer is critical to the functioning of the collar. More specifically, it allows the collar to precisely delineate the fornix and thereby deviate it and support it alongside the vaginal wall. To understand how the stabilizer is necessary, consider what happens when the collar is used alone. The collar 10 is inserted via the vagina 107, and the rim 13 is positioned around the cervix 103 to receive the cervix 103 through the opening 11a. However, the collar 10 alone does not provide sufficient force to accurately define the vaginal fornix 100. Instead, a gap may be present between the outer rim surface 13d and the fornix 101. In conventional devices, this gap may result in an inaccurate estimate of the location of the fornix 101 and as a result lead to vaginal shortening or damage of nearby vital organs.

FIG. 11A illustrates the stabilizer 20 positioned within the collar 10 prior to applying a force to press the collar 10 against to the intra-vaginal fornix 101. Here, the ends 22a of the stabilizer 20 may be inserted into the insertion end 12 of the collar 10. Alternatively, the stabilizer and collar may exist as one piece. The ends may be shaped to define a circle corresponding to a circular shape of the rim 13, as explained in FIG. 12.

FIG. 11B illustrates the stabilizer 20 positioned within the collar 10 after applying the force. When the force is applied by the stabilizer 20 to the inside surface 13e of the rim 13 to press the collar 10 towards the fornix 101, the outer surface 13d of the rim 13 is pressed close to the fornix 101. A bulge is formed at a location corresponding to an intra-abdominal fornix 113, or to the fornix 100 as viewed from the abdominal cavity 111. A surgeon may then accurately estimate the location of the fornix 100 by determining the position of the bulge.

Without the stabilizer, the collar does not precisely delineate the fornix which can lead to vaginal shortening, in the best case scenario, and damage to other vital organs in the worst scenario.

In addition, the pronged design of the stabilizer in conjunction with the dome or trapezoidal shape of the collar allows cervical access through the operation. That is, a tenaculum can be inserted into the vagina alongside a uterine shaft, and may be maneuvered through the prongs and connecting to base to reach the cervix. The dome expands the vaginal wall to further increase access to the cervix.

Cervical access created by the prongs and dome also minimize the risk of tissue damage when retrieving the cervix from an operation where it is incised (e.g., a hysterectomy). Because a surgeon can attach a tenaculum to the cervix during the operation as mentioned, he may simply pull on the tenaculum when the operation is completed to retrieve it. The ability to attach a tenaculum to the cervix eliminates the risk of tissue injury caused by blind retrieval of the cervix. In contrast, conventional devices block access to the cervix through a cup or a balloon. The fornix manipulator preserves this access.

FIG. 11C illustrates the collar 10 having the two outer rim edges 13a and 13f being pressed against the intra-vaginal fornix 101. As illustrated in FIG. 11C, when the stabilizer 20 presses against the rim edges 13a and 13f of collar 10, the fornix 100 distends and a bulge of compressed fornix flesh is visible on the intra-abdominal fornix 113. The gully 13g defined by the rim edges 13a and 13f corresponds to the location of the intra-vaginal fornix 101, so that a surgeon may sense the location of the fornix 100 by prodding the bulge until the gully 13g is detected.

The shape of the trough 13g on the outside of the wall 14 of the collar 10 may form an inner trough 13h on the inside of the collar 10. The ends 22a of the stabilizer 20 may be located within the inner trough 13h. As described above, when the rim 13 is located at the intra-vaginal fornix 101, the trough 13g may be used to guide a surgeon to make an incision at the fornix 100, thereby maximizing the remaining the length of the remaining vaginal wall 102. In other words, by cutting tissue at the fornix 100, the amount of vaginal wall 102 remaining after a surgery may be maximally preserved.

FIG. 12 illustrates the circle E defined by the shape of the ends 22a of the prongs 22. The prongs 22 may have a rounded shape, and a curve of the ends 22a may define a circle E having a diameter d1. While FIG. 12 illustrates two ends 22a, any number of prongs 22 may be used. In addition, the ends 22a may be straight, short, or have any other shape, and the circle E may be defined by center points of the ends 22a.

Figure 13A:
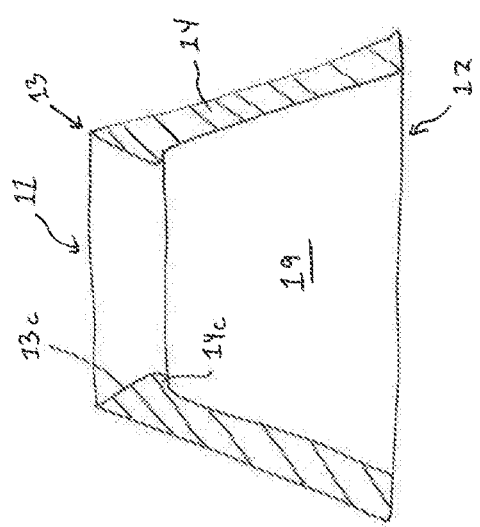
Figure 13D:
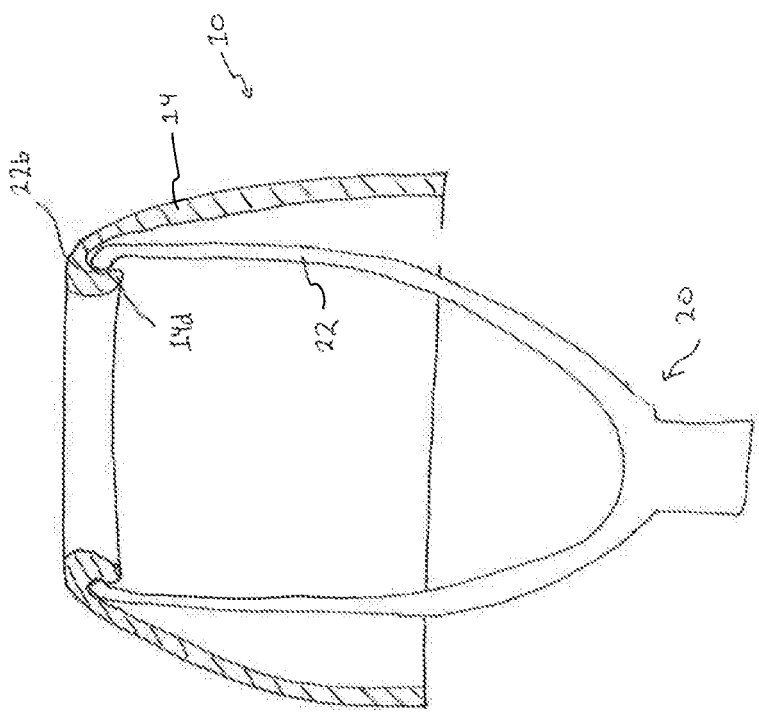
Figure 13C:
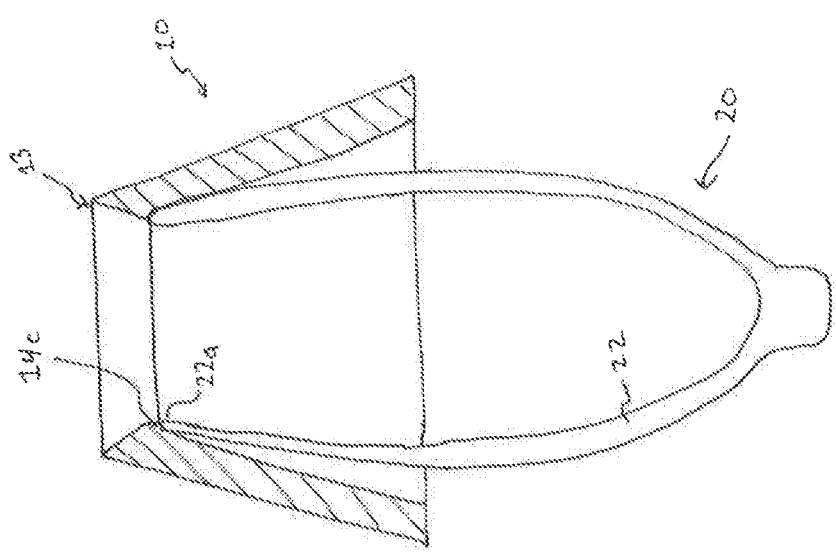

FIGS. 13A to 13C illustrate different configurations of rims 13 of the collar 10. In FIG. 13A, the rim surface 13c includes a protrusion 14c that protrudes inward toward the cavity 19 with respect to the wall 14. The protrusion 14c may be rounded as illustrated in FIG. 13A, or may have an angular shape or any other appropriate shape. The protrusion 14c may form a ridge with respect to the inside of the wall 14, so that the ends 22a of the prongs 22 may abut into the ridge when the prongs 22 are inserted into the collar 10 from the receiving end 12.

FIG. 13B illustrates a ridge 14d having a hook shape, so that the ridge 14d surrounds the entire end 22a of the prongs 22 when the prongs 22 are inserted into the crook defined by the ridge 14d. This allows the prongs to snap into the rim.

FIG. 13C illustrates the stabilizer 20 inserted into the collar 10. The stabilizer 20 is inserted, prong-first, into the collar 10 and the ends 22a of the prongs 22 press against the ridge 14c. Consequently, when force is applied to the stabilizer 20, the stabilizer 20 may transfer the force to the rim 13 of the collar 10.

FIG. 13D illustrates the hook-shaped ridge 14d having a protrusion to interlock with a protrusion 22b at an end 22a of the prongs 22. This may allow the prongs 22 to be attached to the collar 10 by snapping into place temporarily or permanently. Alternatively, the ridge 14d may include a recess to receive a protrusion from the prongs 22.

Figure 14A:
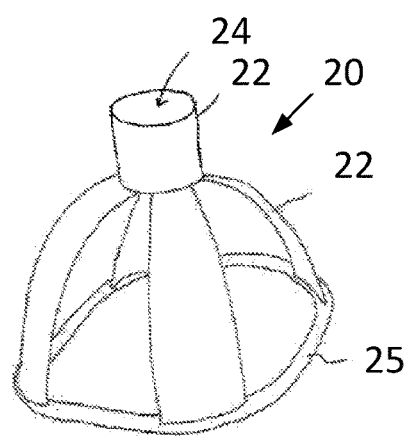
FIGS. 14A and 14B illustrate a stabilizer according to another embodiment of the present general inventive concept.
Figure 14B:
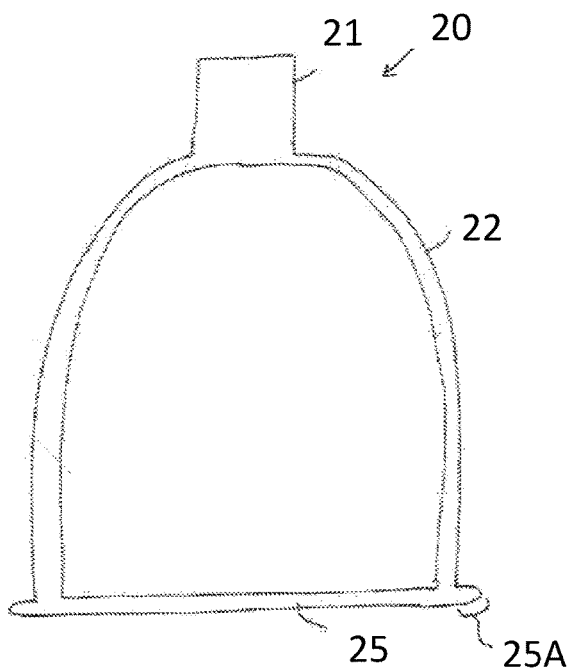

FIGS. 14A and 14B illustrate a stabilizer 20 having a rim 25 at the ends 22a of the prongs 22. The rim 25 may have a substantially flat surface or a rounded surface. The rim 25 may connect each of the prongs 22 and may have a substantially circular shape to correspond to the shape of the opening of the collar 10 and fit underneath the rim 13 of the collar 10. When the stabilizer 20 is pushed against the collar 10, the rim 25 distributes the force of the prongs 22 evenly against the rim 13 of collar 10, thereby creating more even pressure around the intra-vaginal fornix 101. Evenly distributed pressure around the intra-vaginal fornix 101 creates a more evenly distributed bulge of distended fornix flesh visible at the intra-abdominal fornix 113. As illustrated in FIG. 14B, the rim 25 may have an outer rim portion 25a to extend past an outer surface of the prongs 22. The outer circumference of the outer rim portion 25a may conform to an inner circumference of the inside wall of the collar 10.

The rim 25 may be formed of semi-rigid or rigid material. The material may be semi-rigid to allow compression when removing the device from the vaginal canal after the medical procedure.

Figure 15C:
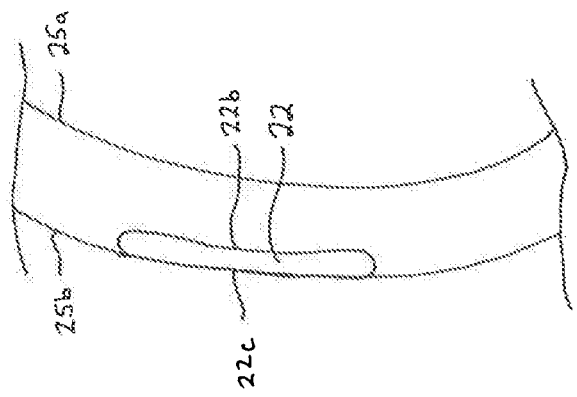
FIGS. 15A to 15D illustrate a relationship between a prong and a rim of a stabilizer.
Figure 15B:
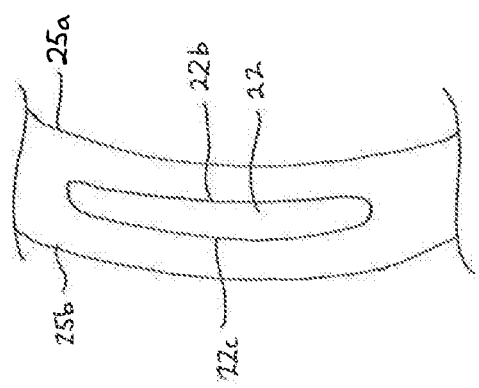
Figure 15A:
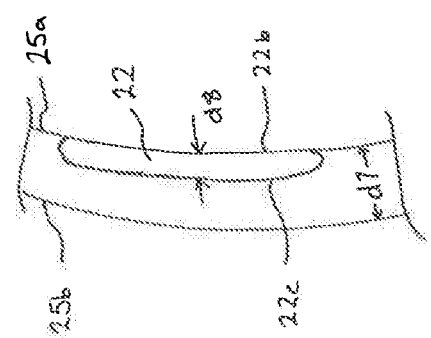

FIGS. 15A to 15D illustrate the rim 25 having different locations with respect to the prongs 22. As illustrated in FIG. 15A, the rim 25 may have a width d7 greater than the width d8 of the prong 22, where the prong 22 contacts the rim 25. The inside edge 25a of the rim 25 may be flush with an inside surface 22b of the prong 22 as illustrated in FIG. 15A. Alternatively, the inside edge 25a and the outside edge 25b of the rim 25 may each extend past the inside surface 22b and outside surface 22c, respectively of the prong 22, as illustrated in FIG. 15B. Alternatively, the outside edge 25b of the rim 25 may be flush with the outside surface 22c of the prong 22 and the inside edge 25a of the rim 25 may extend past the inside surface 22b of the prong 22, as illustrated in FIG. 15C.

Figure 15D:
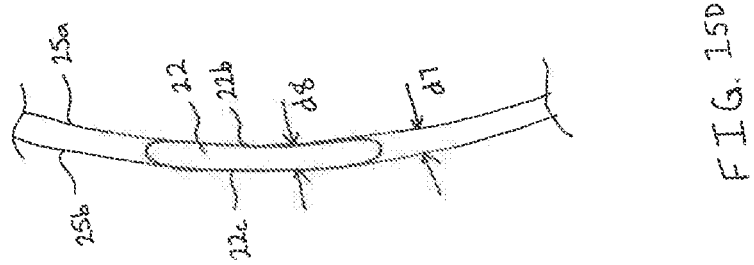

According to yet another alternative, as illustrated in FIG. 15D, the prongs 22 and the rim 25 may have a same width, so that the inside and outside edges 25a and 25b of the rim 25 are each flush with the respective inside and outside surfaces 22b and 22c of the prong 22.

Figure 16:
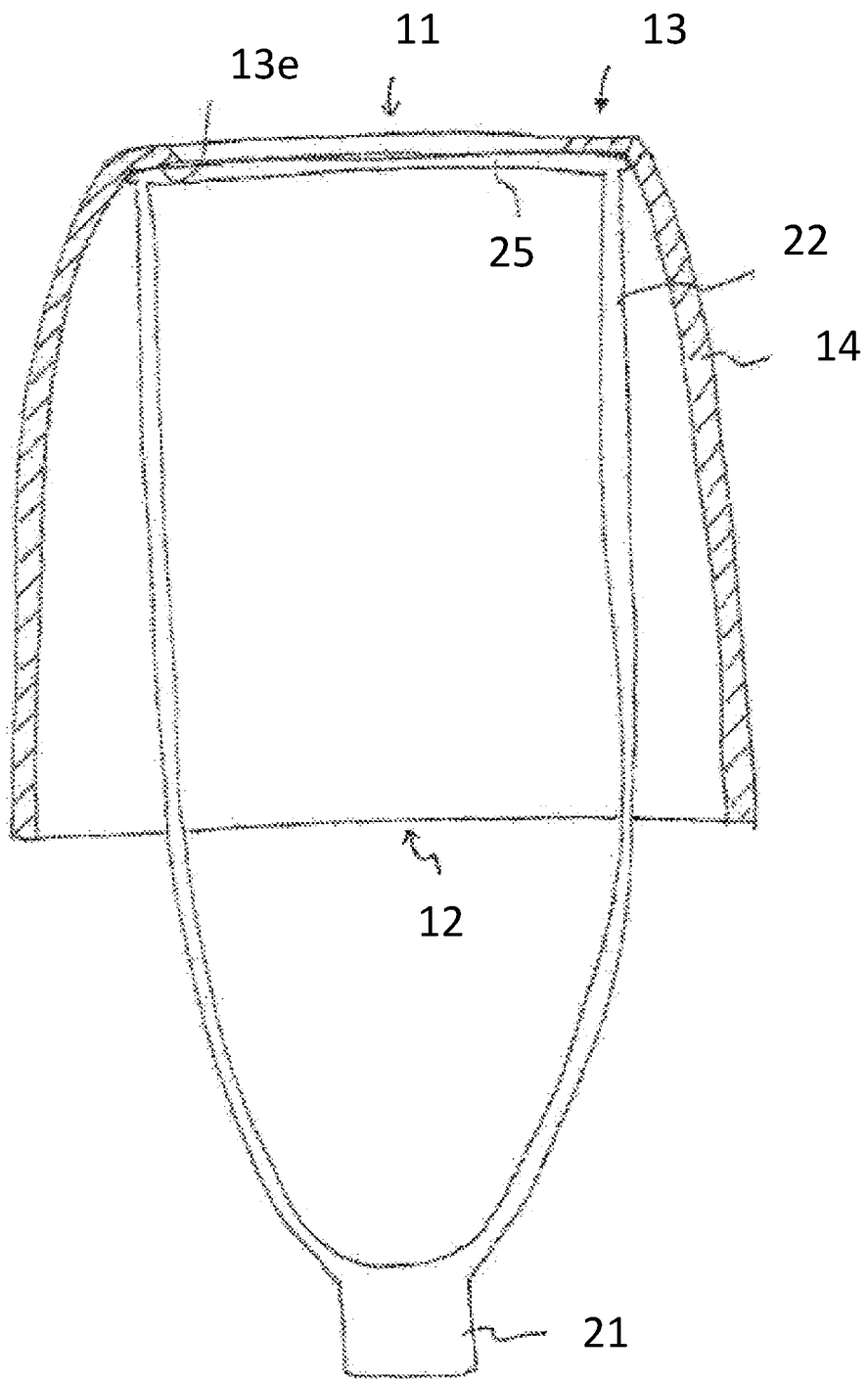
FIG. 16 illustrates a stabilizer having a rim positioned within a collar.

FIG. 16 illustrates the stabilizer 20 positioned within the collar 10. The rim 25 of the stabilizer 20 may press against the inside rim surface 13e of the collar 10. The rim 25 may be fixed to the collar 10, such as with adhesive, welding, or any other bonding method. Alternatively, the rim 25 may not be bonded to the collar 10, and may maintain a position with respect to the collar 10 only by a pressing force against the inside rim surface 13e of the collar 10.

FIGS. 17A to 17D illustrate a stabilizer 20 according to another embodiment of the present general inventive concept. The stabilizer 20 may include a rim 26 connected to the prongs 22. The rim 26 includes an outer edge 26b and an inner edge 26a. The inner edge 26a is located inward from the outer edge 26b in a radial direction, and outward from the outer edge 26 in a linear direction with respect to the base 21 of the stabilizer 20. In other words, the inner edge 26a is offset in an inward direction from the outer edge 26b by a distance d9; and the inner edge 26a is offset in a linear direction from the outer edge 26b with respect to the base 21 by a distance d10. A surface 26c spans between the inner edge 26a and the outer edge 26b. According to one embodiment of the general inventive concept, the surface 16c has a concave shape.

As illustrated in FIG. 17B, when the stabilizer 20 is positioned within the collar 10, the inner edge 26a may be offset from the rim 13 of the collar 10.

Figure 17C:
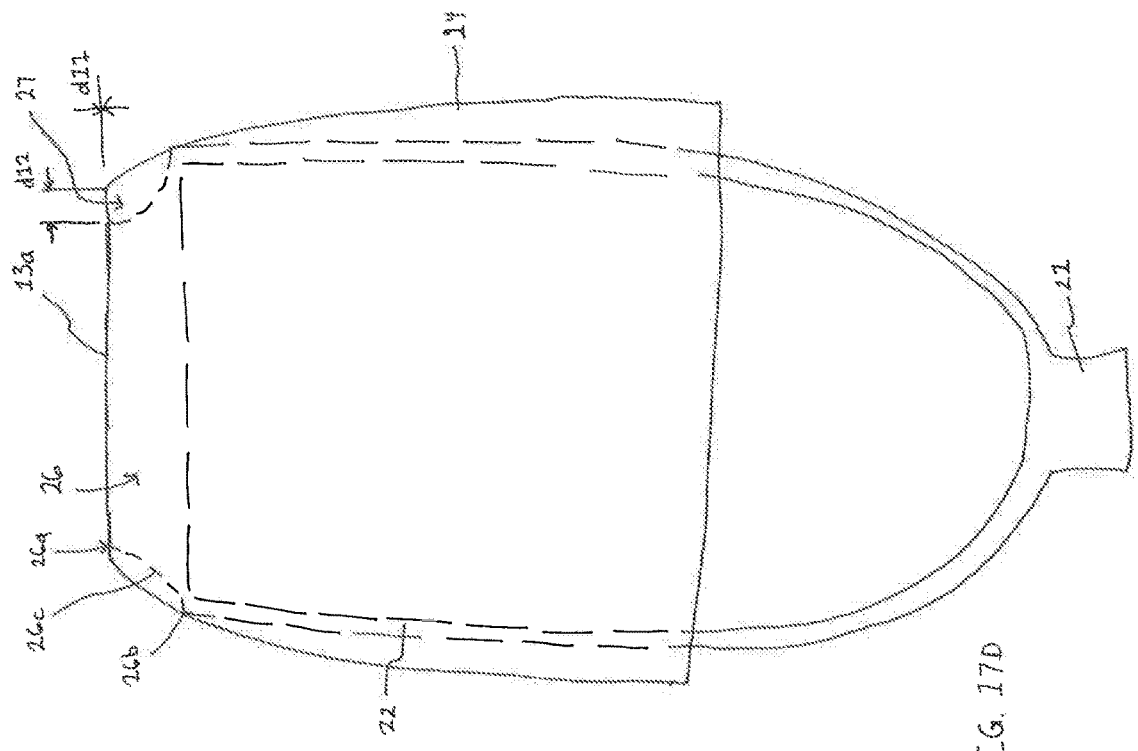

As illustrated in FIG. 17C, the inner edge 26a of the rim 26 may pass through the opening 11a of the contact end 11 of the collar 10. The inner edge 26a may extend past the rim 13 of the collar 10 by a distance d11 in a linear direction with respect to the base 21. In addition, the inner edge 26a may be offset from the outer edge 13a of the collar 10 by a distance d12 in a radial direction. A trough 27 may be formed between the inner edge 26a of the rim 26 and the outer edge 13a of the rim 13 of the collar 10. The trough 27 may be pressed against the intra-vaginal fornix 101, such that a surgeon may locate the vaginal fornix 100 by detecting the location of the trough 27. In other words, the trough 27 formed by the combination of the collar 10 and stabilizer 20 of FIGS. 17A to 17D may act in a manner similar to the trough 13g, described above with respect to FIGS. 8A to 8C.

Figure 17D:
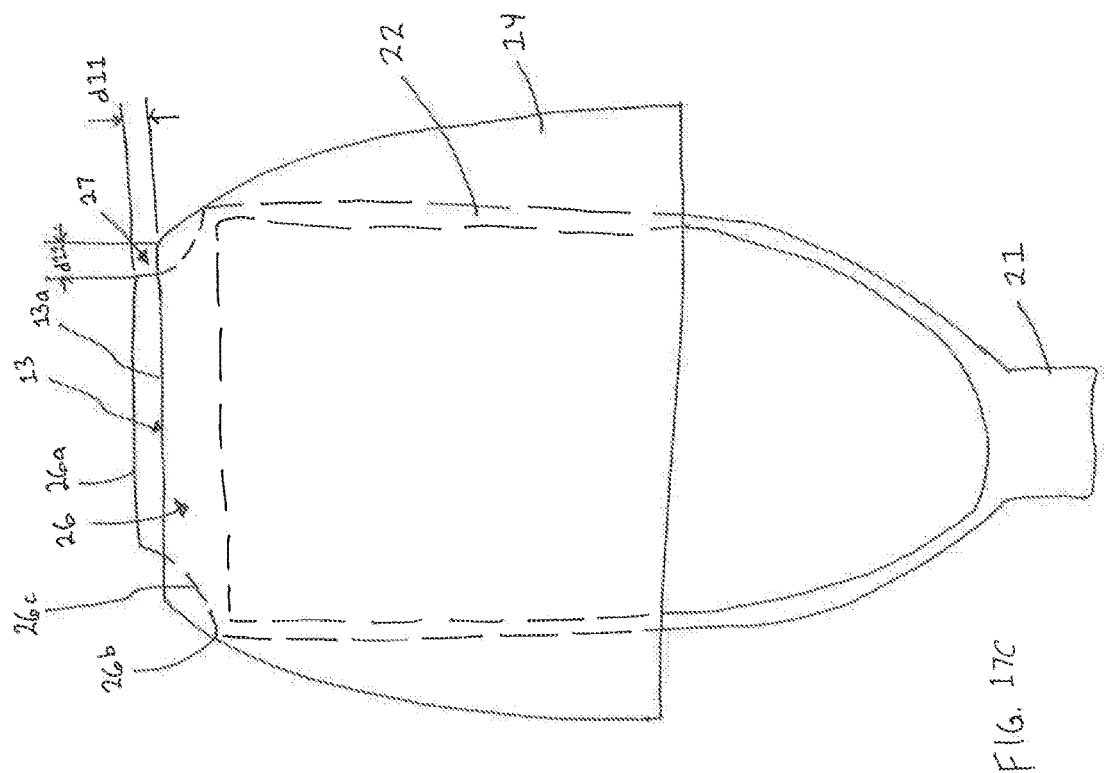

As illustrated in FIG. 17D, the outer edge 13a of the rim 13 of the collar 10 may be substantially flush with the inner edge 26a of the rim 26 of the stabilizer 20. The outer edge 26b of the rim 26 of the stabilizer 20 may contact an inside surface of the wall 14 of the collar to form an offset distance d12 in a radial direction between the inside edge 26a of the rim 26 and the outside edge 13a of the rim 13 of the collar 10. The distance d12 between the edges 26a and 13a may define a trough 27 to indicate to a surgeon the location of the fornix 100, as described above.

The rim 26 may be formed of a rigid to semi-rigid material. The rim 26 and the stabilizer 20 may be fixed to the collar 10 by bonding, latching, sliding, adhesive, welding, or by any other means. Alternatively, the stabilizer 20 may not be fixed with respect to the collar 10, and may be freely removable from the collar 10.

Figure 18B:
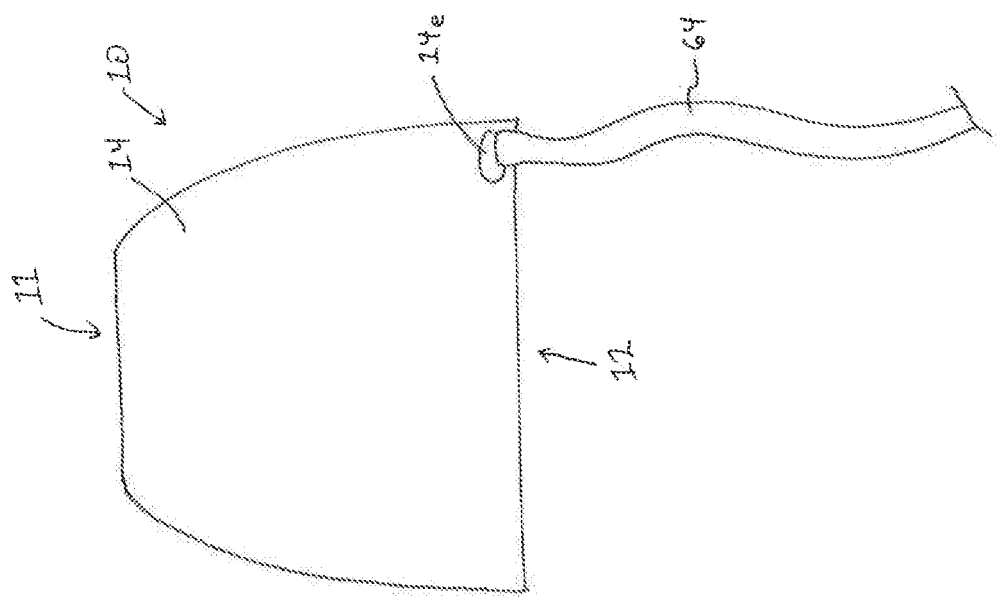
FIGS. 18A and 18B illustrate a strap connection of a collar according to an embodiment of the present general inventive concept.
Figure 18A:
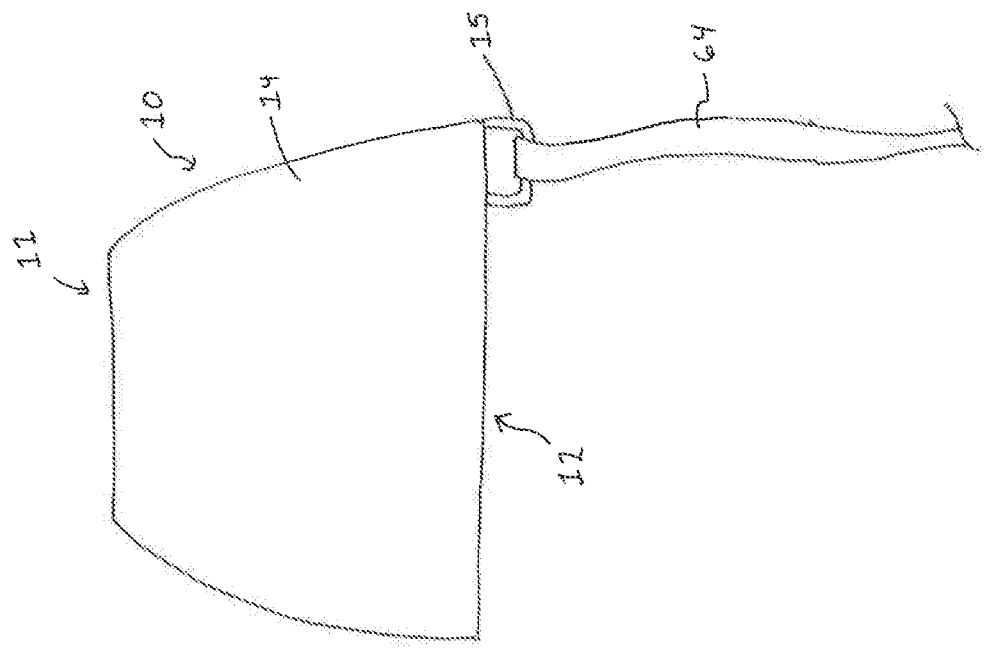

FIGS. 18A and 18B illustrate a strap 64 connected to the collar 10 according to embodiments of the present general inventive concept. As illustrated in FIG. 18A, the collar 10 may include a ring 15, tab, or other protrusion fixed to the collar 10 to which a strap 64 may be attached. The ring 15 may be welded, adhered to, for formed integrally with the wall 14 of the collar 10. When an operation is completed, or when a surgeon desires to remove the collar 10, the surgeon may pull on the strap, and the collar 10 may easily slide down vaginal canal and be removed from a patient's body.

As illustrated in FIG. 18B, a hole 14e may be formed in the collar 10, and the strap 64 may be fixed to the collar 10 by way of the hole 14e. The hole 14e may be located anywhere on the collar.

The strap connected to the first opening of the dome-shaped collar minimizes the risk of tissue injury caused by device retrieval. The surgeon does not have to fish for the device. In addition, when the strap is placed near the contact end 11, the device may be exit the vaginal canal without damaging the vaginal opening. This is because the contact end 11 has a smaller diameter than the receiving end. So when the strap is pulled out of the vaginal canal, the smaller contact end 22 is likely to exit first. This permits vaginal opening to expand to the increasing diameter of the receiving end 12. The alternative, pulling out the receiving end 12 first may damage the tissue if it has a diameter larger than the vaginal opening.

FIG. 19 illustrates the stabilizer 20 and the collar 10 attached to the inner shaft 31 of the uterine manipulator 30. A pressing portion 60 including an outer tube 61, a fixing portion 62, and a screw 63 may also be mounted to the uterine manipulator 30. A handle 32 may be connected to the end of the shaft 31. The handle 32 may include, for example, a control part including an inspection port and controls to move the balloon 35 upward, downward, and sideward, and to inflate and deflate the balloon 35.

The outer tube 61 of the pressing portion 60 may be pressed against the stabilizer 20. The pressing causes the prongs 22 of the stabilizer 20 to and push against rim 13 of collar 10, which causes the rim 13 to press against the intra-vaginal fornix 101 and distend the fornix. When the pressing portion 60 is moved a desired distance along the shaft 31 to generate a desired force, the screw 63 which is mounted to the fixing portion 62 may be tightened to the shaft 31 to fix the pressing portion 60 with respect to the shaft 31.

A strap 64 may be connected between the fixing portion 62 and the collar 10 to allow easy removal of the collar 10 along with the uterine manipulator 30. The collar 10 may include a hole 14e and the strap 64 may be connected to the hole 14e via a ring, a tie, or any other means.

Figure 20B:
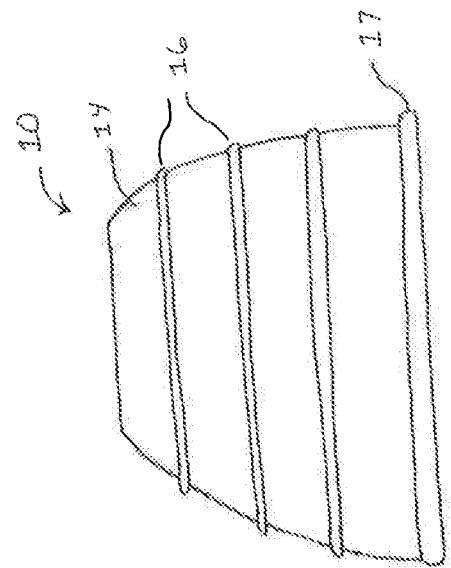
FIGS. 20A and 20B illustrate a collar with ridges.
Figure 20A:
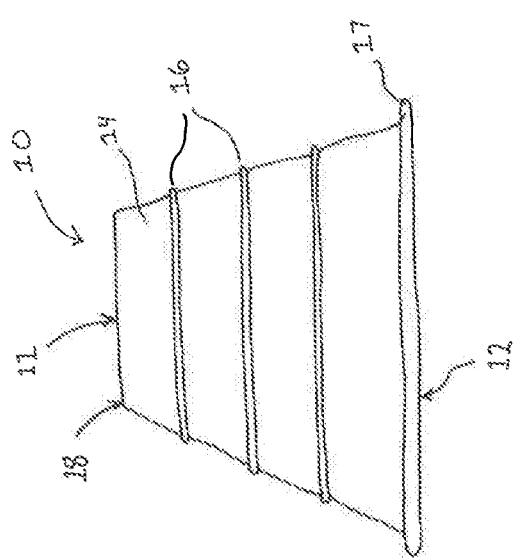

To prevent the tissue of the vaginal canal from moving with respect to the collar 10, the collar 10 may include ridges, as illustrated in FIGS. 20A and 20B. Ridges 16 may be formed on the body of the wall 14. In addition, the collar 10 may include an additional ridge 17 at the receiving end 17 of the collar 10.

The ridges 16 and 17 may prevent the tissue from retracting from the contact end 11 of the collar 10 toward the receiving end 12 when the fornix at the rim 13 is cut. The ridges 16 and 17 may engage and grip the tissue to prevent it from retracting. The ridge 17 at the receiving end 12 may be larger than the ridges 16 on the body of the collar 10 so that even if the tissue is able to slide past the smaller ridges 16, the larger ridge 17 may prevent the tissue from sliding past the receiving end 12 of the collar 10.

Ridges 16 and 17 coupled with the dome shaped collar 10 minimize abdominal disinflation. The increasing diameter of the collar 10 makes it difficult for the tissue to retract from the contact end 11 to the receiving end 12. Likewise, the ridges 16 and 17 may prevent tissue from sliding. As a result, a seal may be formed between tissue of the vaginal wall 102 and the collar 10 even after the fornix is incised.

The ridges 16 and 17 may be made of the same material as the collar 10 or of another material applied to the collar 10 after the collar 10 is fabricated. The ridges 16 and 17 may have rough surfaces relative to the outside surface of the collar 10. The ridges 16 and 17 may be concentric circles parallel to each other. The ridges may be broken circles having gaps between raised portions, or unbroken circles.

As described above, a fornix manipulator according to the present general inventive concept accurately delineates, deviates and supports the vaginal fornix even when a shape and/or size of a cervix may be unusual. Its dome shape and ridges maintain a seal in the abdominal cavity even after an incision is made in the vaginal fornix or vaginal wall. In addition, the dome shape allows for precise delineation; provides a platform for the dissection of organs adjacent to the vaginal wall; expands the vaginal wall for maximal cervical access; and its increasing diameter minimizes the risk of injury during device insertion and retrieval if attached to a strap. The manipulator's open-ended collar in combination with the stabilizer preserve access to the cervix through the operation, allowing a surgeon to attach tenaculums to the cervix to avoid blind cervix retrieval and tissue damage. In addition, the stabilizer also allows for precise fornix delineation by pressing the rim of the collar to the fornix. This maximizes delineation, deviation, support, while also minimizing the risk of vaginal shortening and injury to other vital organs. In addition, the fornix manipulator provides an accurate guide for a surgeon to make an incision by providing a gully at a location of the vaginal fornix. Other features and/or utilities of the present general inventive concept would be apparent to one having ordinary skill in the art and are not limited to the above-described features and/or utilities.

Although a few embodiments of the present general inventive concept have been shown and described, it would be appreciated by those skilled in the art that changes may be made in these embodiments without departing from the principles and spirit of the general inventive concept, the scope of which is defined in the claims and their equivalents.

What is claimed is:

1. A collar, comprising:
a first end including a rim to define a first opening adapted to receive a cervix, the first end having a first diameter positioned on a distal end of the collar, the first end having a first outer rim edge and a second outer rim edge, wherein a gully is positioned between the first outer rim edge and the second outer rim edge, wherein the first diameter extends across the first outer rim edge, wherein the second outer rim edge has a second outer rim edge diameter that is larger than the first diameter, wherein the second outer rim edge does not extend past a plane defined by the first outer rim edge, wherein the gully does not extend past a plane defined by the second outer rim edge;
a second end having a second opening and having a second diameter greater than the first diameter, the second end being positioned on a proximal end of the collar; and
a side wall between the first end and the second end to define an inner cavity between the first opening and the second opening,
the collar having an inner surface adapted to contact a cervix and an outer surface adapted to contact a vaginal wall, wherein the second end is configured to be positioned away from the cervix when the inner surface of the collar contacts the cervix;
wherein the first end and second end form opposing ends of a hollow tunnel adapted to receive the cervix.

2. The collar of claim 1, wherein the rim of the first end is adapted to circumscribe the vaginal fornix.

3. The collar of claim 1, wherein the collar has one of a trapezoid cross-section shape, a domed cross-section shape, or a combination of a trapezoid and domed cross-section shape.

4. The collar of claim 1, further comprising a plurality of parallel ridges located around an outside surface of the side wall.

5. The collar of claim 1, wherein the collar has a one of a hole, ring, tab, or other protrusion fixed to the collar to receive a strap.

6. The collar of claim 1, wherein the collar includes a protrusion.

7. The collar of claim 1, wherein the rim surface has one of a concave and a convex shape.

8. A collar comprising:
(a) a first end having a first opening with a first diameter and adapted to receive a cervix, the first diameter being positioned on a distal end of the collar, the first end having a first outer rim edge and a second outer rim edge, wherein a gully is positioned between the first outer rim edge and the second outer rim edge, wherein the first diameter extends across the first outer rim edge, wherein the second outer rim edge has a second outer rim edge diameter that is larger than the first diameter, wherein the second outer rim edge does not extend past a plane defined by the first outer rim edge, wherein the gully does not extend past a plane defined by the second outer rim edge;
(b) a second end having a second opening with a second diameter greater than the first end, the second end being positioned on a proximal end of the collar,
(c) an inner surface adapted to contact a cervix and (d) an outer surface adapted to contact a vaginal wall, wherein the second end is configured to be positioned away from the cervix when the inner surface of the collar contacts the cervix;
wherein the first opening and second opening form opposing ends of a hollow tunnel adapted to receive the cervix.

9. The collar of claim 8, comprising ridges around the outer surface of the collar.

10. The collar of claim 8, wherein the collar has one of a trapezoid cross-section shape, a domed cross-section shape, or a combination of a trapezoid and domed cross-section shape.

11. The collar of claim 8, wherein the collar has one of a hole, ring, tab, or other protrusion fixed to the collar to receive a strap.

12. The collar of claim 8, wherein the second opening is encircled by a second rim.

13. The collar of claim 8, wherein the rim surface has one of a concave and a convex shape.

14. The collar of claim 8, wherein the collar includes a protrusion.

* * * * *